(12) United States Patent
Su et al.

(10) Patent No.: US 11,793,775 B2
(45) Date of Patent: Oct. 24, 2023

(54) COMBINED THERAPY FOR TREATING ALZHEIMER'S DISEASE

(71) Applicants: MERRY LIFE BIOMEDICAL COMPANY, LTD., Tainan (TW); NATIONAL HEALTH RESEARCH INSTITUTES, Miaoli County (TW)

(72) Inventors: Ih-Jen Su, Tainan (TW); Feng-Shiun Shie, Chung-He (TW)

(73) Assignees: MERRY LIFE BIOMEDICAL COMPANY, LTD., Tainan (TW); NATIONAL HEALTH RESEARCH INSTITUTES, Miaoli (TW)

( * ) Notice: Subject to any disclaimer, the term of this patent is extended or adjusted under 35 U.S.C. 154(b) by 27 days.

(21) Appl. No.: 17/659,974

(22) Filed: Apr. 20, 2022

(65) Prior Publication Data
US 2022/0362180 A1 Nov. 17, 2022

Related U.S. Application Data

(60) Provisional application No. 63/177,213, filed on Apr. 20, 2021.

(51) Int. Cl.
*A61K 31/165* (2006.01)
*C07K 16/00* (2006.01)
*C07K 16/18* (2006.01)

(52) U.S. Cl.
CPC ............ *A61K 31/165* (2013.01); *C07K 16/18* (2013.01)

(58) Field of Classification Search
CPC ............ A61K 31/165; A61K 2039/505; C07K 16/18; A61P 25/28
See application file for complete search history.

(56) References Cited

U.S. PATENT DOCUMENTS

2019/0290604 A1* 9/2019 Su .................... A61K 31/165

OTHER PUBLICATIONS

Carabotti et al., "The gut-brain axis: interactions between enteric microbiota, central and enteric nervous systems," Ann Gastroenterol. Apr.-Jun. 2015;28(2):203-209.
Claesson et al., "Gut microbiota composition correlates with diet and health in the elderly," Nature. Aug. 9, 2012;488(7410):178-84.
Cummings J, et al., "Alzheimer's Disease drug development pipeline: 2018," Alzheimer's Dement (N Y). 2018;4:195-214.
Dheen et al., "Microglial Activation and its Implications in the Brain Diseases," Curr Med Chem. 2007;14,1189-1197.
Erny et al., "Host microbiota constantly control maturation and function of microglia in the CNS," Nat. Neurosci. Jul. 2015;18(7):965-977.
Fillit et al., "Aducanumab and the FDA—where are we now?" Nat Rev Neurol. Jan. 13, 2021. doi: 10.1038/s41582-020-00454-9.
Geerts et al., "Learning from amyloid trials in Alzheimer's disease. A virtual patient analysis using a quantitative systems pharmacology approach," Alzheimer's Dement. Jun. 2020;16(6):862-872.
Gregori et al., "Nanomedicine for the treatment of Alzheimer's disease," Nanomedicine. 2015;10(7):1203-18.
Hsu et al., "Primary and Secondary Prevention Trials in Alzheimer Disease: Looking Back, Moving Forward," Curr Alzheimer Res. 2017;14(4):426-440.
Jack et al., "NIA-AA Research Framework: Toward a biological definition of Alzheimer's disease," Alzheimer's Dement. Apr. 2018;14(4):535-562.
Knopman et al., "Failure to demonstrate efficacy of aducanumab: An analysis of the EMERGE and ENGAGE trials as reported by Biogen, Dec. 2019," Alzheimer's Dement. 2020. doi: 10.1002/alz.12213.
Ling et al., "Structural and Functional Dysbiosis of Fecal Microbiota in Chinese Patients with Alzheimer's Disease," Front Cell Dev Biol. Feb. 4, 2021;8:634069.
Liu et al., "Role of Microglia in Inflammation-Mediated Neurodegenerative Diseases: Mechanisms and Strategies for Therapeutic Intervention," J Pharmacol Exp Ther. 2003,304,1-7.
Matcovitch-Natan et al., "Microglia development follows a stepwise program to regulate brain homeostasis," Science Aug. 19, 2016;353(6301): aad8670.
Michaud et al., "Anti-inflammatory Signaling in Microglia Exacerbates Alzheimer's Disease-Related Pathology," Neuron. Feb. 4, 2015;85(3):450-2.
Perry et al., "Microglia in neurodegenerative disease," Nat Rev Neurol. 2010;6:193-201.
Shie et al., Synergistic effects of an innovative combination therapy on treating Alzheimer's disease involving modulation of gut dysbiosis. Alzheimer's Dement. 2020; 16(Suppl. 9):e045139.
Silva et al., "The Role of Short-Chain Fatty Acids From Gut Microbiota in Gut-Brain Communication," Front Endocrinol (Lausanne). 2020; 11: 25.
Sun et al., "Effect of Clostridium butyricum against Microglia-Mediated Neuroinflammation in Alzheimer's Disease via Regulating Gut Microbiota and Metabolites Butyrate," Mol Nutr Food Res. Jan. 2020; 64(2): e1900636.

(Continued)

*Primary Examiner* — Jeanette M Lieb
(74) *Attorney, Agent, or Firm* — Prosyla Group PC

(57) ABSTRACT

The disclosure provides a therapeutic method for preventing, ameliorating and/or treating Alzheimer's disease in a subject in need of such treatment. The therapeutic method comprises administrating to said subject a pharmaceutical combination comprising an effective amount of curcumin analog, TML-6 and an effective amount of an anti-A beta (Aβ) antibody.

18 Claims, 15 Drawing Sheets
Specification includes a Sequence Listing.

(56) References Cited

OTHER PUBLICATIONS

Vandevrede et al., "Symptomatic amyloid-related imaging abnormalities in an APOE ϵ4/ϵ4 patient treated with aducanumab," Alzheimers Dement (Amst). Oct. 9, 2020;12(1):e12101.
Vogt et al., "Gut microbiome alterations in Alzheimer's disease," Sci Rep. Oct. 19, 2017; 7(1):13537.
Yan et al., "Targeting the β secretase BACE1 for Alzheimer's disease therapy," Lancet Neurol. 2014;13(3):319-29.

\* cited by examiner

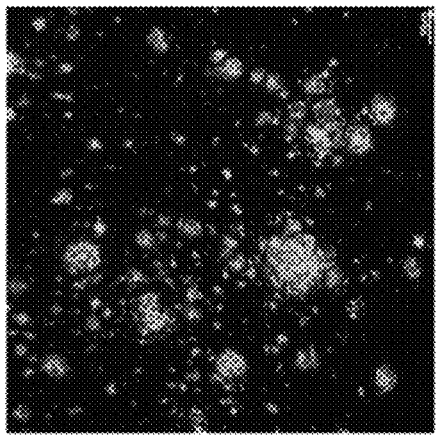
Fig. 1B
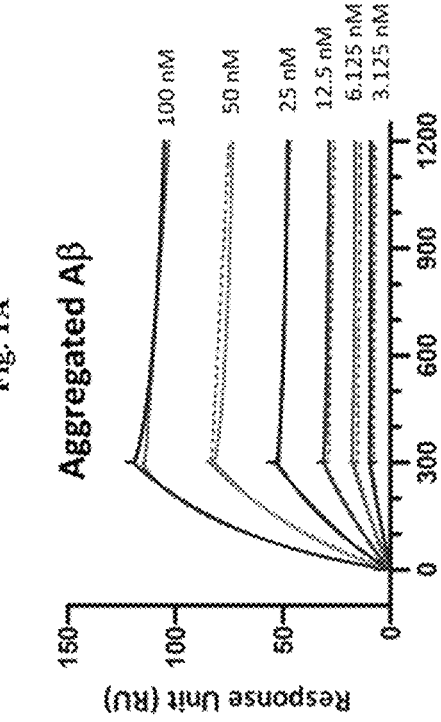
Fig. 1D
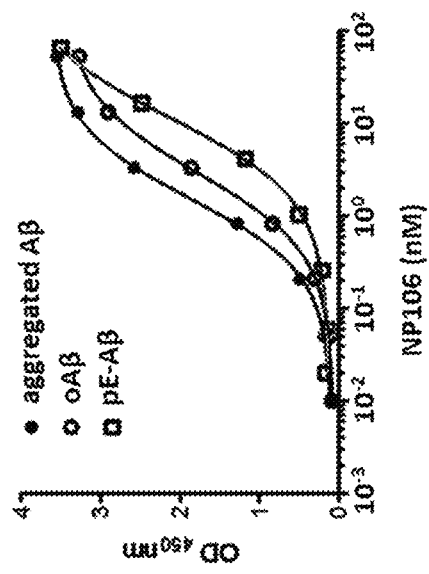
Fig. 1A
Fig. 1C

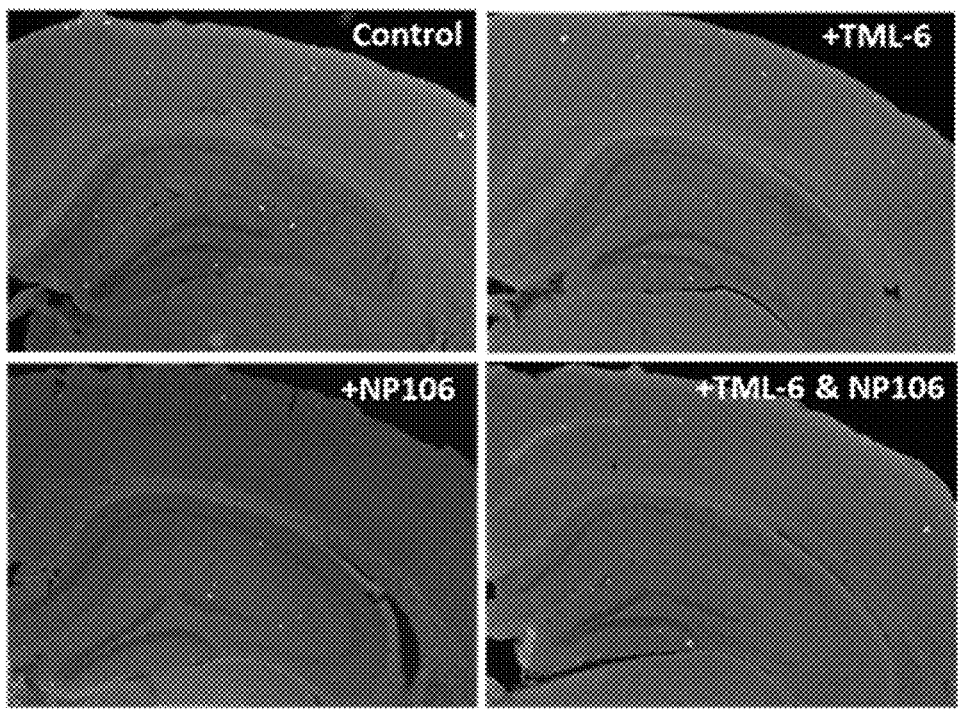
Fig. 2A
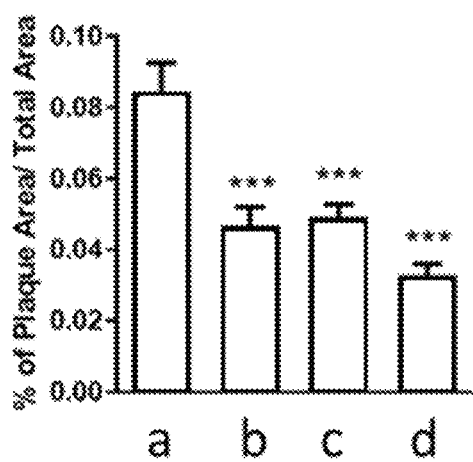
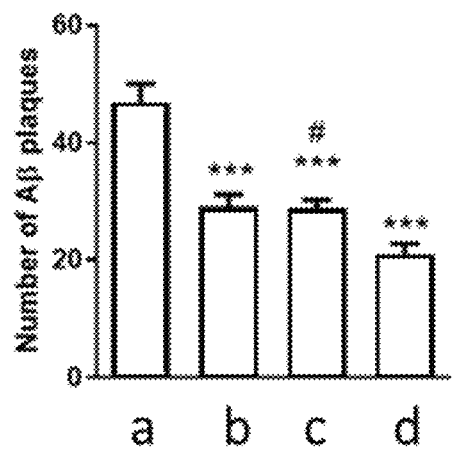
Fig. 2B  Fig. 2C
a, APP/PS1 control; b, APP/PS1+TML-6;
c, APP/PS1+NP106; d, APP/PS1+TML-6&NP106 a, APP/PS1 control; b, APP/PS1+TML-6;
c, APP/PS1+NP106; d, APP/PS1+TML-6&NP106

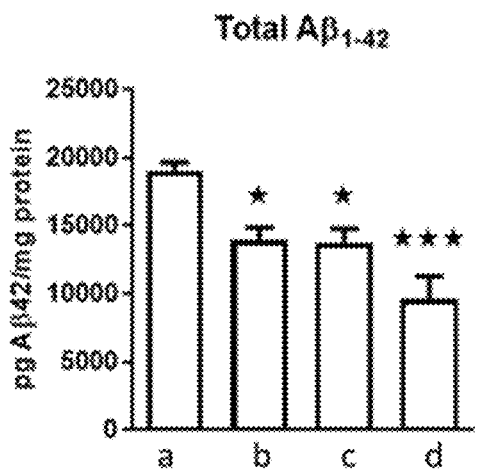
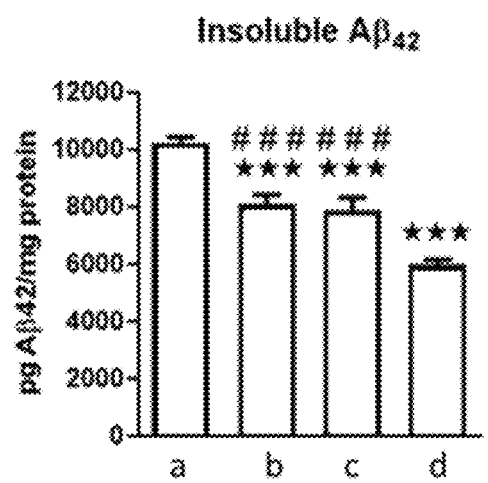
Fig. 3A　　　　　　　　　　Fig. 3B
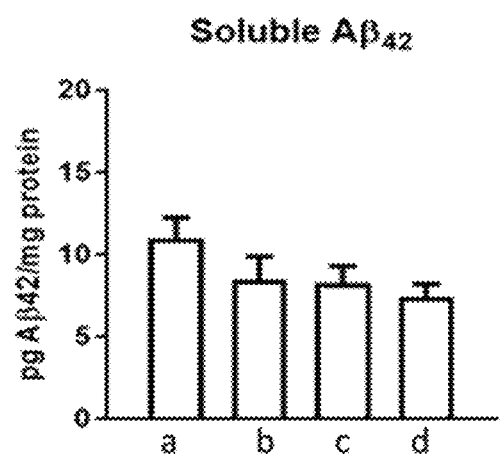
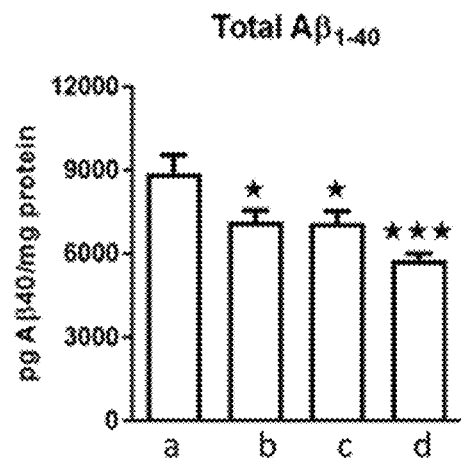
Fig. 3C　　　　　　　　　　Fig. 3D
a, APP/PS1 control; b, APP/PS1+ TML-6;
c, APP/PS1+NP106; d, APP/PS1+TML-6&NP106;

a, APP/PS1 control; b, APP/PS1+TML-6;

c, APP/PS1+NP106; d, APP/PS1+TML-6&NP106 a: APP/PS1 control
b: APP/PS1+TML-6
c: APP/PS1+NP106
d: APP/PS1+TML-6&NP106

A = wt    B = APP/PS1 control    C = APP/PS1 + TML-6
D = APP/PS1 + NP106    E = APP/PS1 + TML-6 & NP106

A = wt    B = APP/PS1 control    C = APP/PS1 + TML-6
D = APP/PS1 + NP106    E = APP/PS1 + TML-6 & NP106

A = wt   B = APP/PS1 control   C = APP/PS1 + TML-6
D = APP/PS1 + NP106   E = APP/PS1 + TML-6 & NP106

SEQUENCE LISTING

```
<160> NUMBER OF SEQ ID NOS: 27

<210> SEQ ID NO 1
<211> LENGTH: 17
<212> TYPE: PRT
<213> ORGANISM: Artificial Sequence
<220> FEATURE:
<223> OTHER INFORMATION: synthetic construct

<400> SEQUENCE: 1

Cys Arg Ser Ser Gln Thr Ile Val His Ser Asn Gly Asn Thr Tyr Leu
1               5                   10                  15

Glu

<210> SEQ ID NO 2
<211> LENGTH: 7
<212> TYPE: PRT
<213> ORGANISM: Artificial Sequence
<220> FEATURE:
<223> OTHER INFORMATION: synthetic construct

<400> SEQUENCE: 2

Lys Val Ser Asn Arg Phe Ser
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic construct

<400> SEQUENCE: 3

Phe Gln Gly Ser His Val Pro Leu Thr
1               5

<210> SEQ ID NO 4
<211> LENGTH: 7
<212> TYPE: PRT
<213> ORGANISM: Artificial Sequence
<220> FEATURE:
<223> OTHER INFORMATION: synthetic construct

<400> SEQUENCE: 4

Thr Ser Gly Met Asn Val Gly
1               5

<210> SEQ ID NO 5
```

```
<211> LENGTH: 16
<212> TYPE: PRT
<213> ORGANISM: Artificial Sequence
<220> FEATURE:
<223> OTHER INFORMATION: synthetic construct

<400> SEQUENCE: 5

His Ile Trp Trp Asp Asp Asp Lys Tyr Tyr Asn Pro Ser Leu Lys Ser
1               5                   10                  15

<210> SEQ ID NO 6
<211> LENGTH: 12
<212> TYPE: PRT
<213> ORGANISM: Artificial Sequence
<220> FEATURE:
<223> OTHER INFORMATION: synthetic construct

<400> SEQUENCE: 6

Arg Arg Ser Ile Arg Gly Ser Asp Tyr Phe Asp Tyr
1               5                   10

<210> SEQ ID NO 7
<211> LENGTH: 17
<212> TYPE: PRT
<213> ORGANISM: Artificial Sequence
<220> FEATURE:
<223> OTHER INFORMATION: synthetic construct

<400> SEQUENCE: 7

Cys Arg Ser Ser Gln Ser Ile Val His Ser Asn Gly Asn Thr Tyr Leu
1               5                   10                  15

Glu

<210> SEQ ID NO 8
<211> LENGTH: 9
<212> TYPE: PRT
<213> ORGANISM: Artificial Sequence
<220> FEATURE:
<223> OTHER INFORMATION: synthetic construct

<400> SEQUENCE: 8

Phe Gln Gly Ser Leu Val Pro Leu Thr
1               5

<210> SEQ ID NO 9
<211> LENGTH: 7
<212> TYPE: PRT
<213> ORGANISM: Artificial Sequence
<220> FEATURE:
<223> OTHER INFORMATION: synthetic construct

<400> SEQUENCE: 9

Thr Ser Gly Met Gly Val Gly
1               5

<210> SEQ ID NO 10
<211> LENGTH: 14
<212> TYPE: PRT
<213> ORGANISM: Artificial Sequence
<220> FEATURE:
<223> OTHER INFORMATION: synthetic construct

<400> SEQUENCE: 10

Arg Arg Ala Leu Arg Asn Val Val Ala Asp Ala Met Asp Tyr
1               5                   10
```

-continued

```
<210> SEQ ID NO 11
<211> LENGTH: 7
<212> TYPE: PRT
<213> ORGANISM: Artificial Sequence
<220> FEATURE:
<223> OTHER INFORMATION: synthetic construct

<400> SEQUENCE: 11

Thr Ser Ala Val Gly Val Ser
1               5

<210> SEQ ID NO 12
<211> LENGTH: 16
<212> TYPE: PRT
<213> ORGANISM: Artificial Sequence
<220> FEATURE:
<223> OTHER INFORMATION: synthetic construct

<400> SEQUENCE: 12

His Ile Tyr Trp Asp Asp Asp Lys Arg Tyr Asn Pro Ser Leu Lys Ser
1               5                   10                  15

<210> SEQ ID NO 13
<211> LENGTH: 14
<212> TYPE: PRT
<213> ORGANISM: Artificial Sequence
<220> FEATURE:
<223> OTHER INFORMATION: synthetic construct

<400> SEQUENCE: 13

Arg Arg Pro Tyr Tyr Arg Tyr Asp Val Asp Ala Met Asp Tyr
1               5                   10

<210> SEQ ID NO 14
<211> LENGTH: 17
<212> TYPE: PRT
<213> ORGANISM: Artificial Sequence
<220> FEATURE:
<223> OTHER INFORMATION: synthetic construct

<400> SEQUENCE: 14

Cys Arg Ser Ser Gln Asn Ile Val His Ser Asn Gly Asn Thr Tyr Leu
1               5                   10                  15

Glu

<210> SEQ ID NO 15
<211> LENGTH: 7
<212> TYPE: PRT
<213> ORGANISM: Artificial Sequence
<220> FEATURE:
<223> OTHER INFORMATION: synthetic construct

<400> SEQUENCE: 15

Thr Val Ser Asn Arg Phe Ser
1               5

<210> SEQ ID NO 16
<211> LENGTH: 7
<212> TYPE: PRT
<213> ORGANISM: Artificial Sequence
<220> FEATURE:
<223> OTHER INFORMATION: synthetic construct

<400> SEQUENCE: 16

Ser Ser Val Leu Gly Val Ser
1               5
```

```
<210> SEQ ID NO 17
<211> LENGTH: 16
<212> TYPE: PRT
<213> ORGANISM: Artificial Sequence
<220> FEATURE:
<223> OTHER INFORMATION: synthetic construct

<400> SEQUENCE: 17

His Ile Tyr Trp Asp Asp Asp Arg Arg Tyr Asn Pro Ser Leu Lys Ser
1               5                   10                  15

<210> SEQ ID NO 18
<211> LENGTH: 14
<212> TYPE: PRT
<213> ORGANISM: Artificial Sequence
<220> FEATURE:
<223> OTHER INFORMATION: synthetic construct

<400> SEQUENCE: 18

Arg Arg Gly Lys Met Gly Arg Gly Leu Asp Ala Met Asp Tyr
1               5                   10

<210> SEQ ID NO 19
<211> LENGTH: 16
<212> TYPE: PRT
<213> ORGANISM: Artificial Sequence
<220> FEATURE:
<223> OTHER INFORMATION: synthetic construct

<400> SEQUENCE: 19

His Ile Tyr Trp Asp Asp Asp Arg Arg Tyr Asn Pro Ser Leu Arg Ser
1               5                   10                  15

<210> SEQ ID NO 20
<211> LENGTH: 14
<212> TYPE: PRT
<213> ORGANISM: Artificial Sequence
<220> FEATURE:
<223> OTHER INFORMATION: synthetic construct

<400> SEQUENCE: 20

Arg Arg Gly Lys Met Gly Arg Gly Leu Asp Ala Leu Asp Phe
1               5                   10

<210> SEQ ID NO 21
<211> LENGTH: 9
<212> TYPE: PRT
<213> ORGANISM: Artificial Sequence
<220> FEATURE:
<223> OTHER INFORMATION: synthetic construct

<400> SEQUENCE: 21

Phe Gln Gly Ser Arg Val Pro Leu Thr
1               5

<210> SEQ ID NO 22
<211> LENGTH: 16
<212> TYPE: PRT
<213> ORGANISM: Artificial Sequence
<220> FEATURE:
<223> OTHER INFORMATION: synthetic construct

<400> SEQUENCE: 22

His Ile Trp Trp Asp Asp Asp Lys Tyr Phe Asn Pro Ser Leu Lys Ser
1               5                   10                  15
```

```
<210> SEQ ID NO 23
<211> LENGTH: 12
<212> TYPE: PRT
<213> ORGANISM: Artificial Sequence
<220> FEATURE:
<223> OTHER INFORMATION: synthetic construct

<400> SEQUENCE: 23

Arg Arg Ser Leu Lys Trp Leu Asp Ala Met Asp Tyr
1               5                   10

<210> SEQ ID NO 24
<211> LENGTH: 9
<212> TYPE: PRT
<213> ORGANISM: Artificial Sequence
<220> FEATURE:
<223> OTHER INFORMATION: synthetic construct

<400> SEQUENCE: 24

Phe Gln Ser Ser Arg Val Pro Leu Thr
1               5

<210> SEQ ID NO 25
<211> LENGTH: 7
<212> TYPE: PRT
<213> ORGANISM: Artificial Sequence
<220> FEATURE:
<223> OTHER INFORMATION: synthetic construct

<400> SEQUENCE: 25

Thr Ser Gly Met Gly Val Ser
1               5

<210> SEQ ID NO 26
<211> LENGTH: 16
<212> TYPE: PRT
<213> ORGANISM: Artificial Sequence
<220> FEATURE:
<223> OTHER INFORMATION: synthetic construct

<400> SEQUENCE: 26

His Ile Tyr Trp Asp Asp Asp Lys Ser Tyr Asn Pro Ser Leu Lys Ser
1               5                   10                  15

<210> SEQ ID NO 27
<211> LENGTH: 13
<212> TYPE: PRT
<213> ORGANISM: Artificial Sequence
<220> FEATURE:
<223> OTHER INFORMATION: synthetic construct

<400> SEQUENCE: 27

Arg Arg Arg Asn Trp Val Ile Thr Asp Ala Met Glu Tyr
1               5                   10
```

COMBINED THERAPY FOR TREATING ALZHEIMER'S DISEASE

CROSS-REFERENCE TO RELATED APPLICATIONS

This application claims benefit to and priority to U.S. Provisional Patent Application No. 63/177,213, filed on Apr. 20, 2021, the contents of which are hereby incorporated by reference in their entirety.

SEQUENCE LISTING

The instant application contains a Sequence Listing which is submitted electronically in ASCII format and is hereby incorporated by reference in its entirety. The ASCII copy, created on Aug. 1, 2022, is named "G4590-12300US_Replacement_SeqList_20220801.txt" and is 7 kilobytes in size.

FIELD OF THE DISCLOSURE

This disclosure relates to treatments for Alzheimer's disease. More specifically, the disclosure relates to a combined therapy for treating Alzheimer's disease.

BACKGROUND OF THE DISCLOSURE

Alzheimer's disease (AD) is the most common form of dementia and is characterized by clinical manifestations of progressive memory loss and cognitive dysfunction. While there is no cure for AD, amyloid beta (amyloid-β, Aβ or A beta), the major component Aβ plaques, is one of the most attractive therapeutic targets for treating AD, and many disease-modifying strategies have aimed to prevent Aβ production and/or to enhance its clearance (Yan et al., Lancet Neurol. 2014; 13(3):319-29; Gregori et al., Nanomedicine. 2015; 10(7):1203-18; Hsu et al., Curr Alzheimer Res. 2017;14(4):426-440). Microglia are the major immune cells residing in the brain, and are predominantly responsible for Aβ clearance through their phagocytic activity. Although microglial function can be independent of morphological changes (Perry et al., Nat Rev Neurol. 2010; 6:193-201), microglial morphology can be transformed from a ramified morphology in the healthy condition, in which cells are highly branched with many long processes, to an amoeboid/de-ramified morphology in the activated state. Over-activated microglia during the pathogenesis of AD are amoeboid/de-ramified with enlarged cell bodies in the vicinity of Aβ plaques, which are in their phagocytic phenotype that facilitates the clearance of Aβ. However, chronic over-activation can damage microglial function, leading to "frustrated microglia", which amoeboid microglia are dysfunctional and are unable to execute Aβ phagocytosis (Michaud et al., Neuron. 2015 Feb. 4; 85(3):450-2). Importantly, chronic microglial over-activation deteriorates microglia-activated pro-inflammation and escalating neuroinflammation that has been emerging as determinant in the progression of AD (Liu et al., J Pharmacol Exp Ther. 2003, 304, 1-7; Dheen et al., Curr Med Chem. 2007; 14, 1189-1197).

Emerging evidence indicate that AD is a multifactorial neurodegenerative disease, and monotherapy may be insufficient to treat AD. The need of a treatment regimen with multifaceted functions provides a rationale for a combination treatment to enhance the therapeutic efficacy.

SUMMARY OF THE DISCLOSURE

A combination strategy for treating AD is achieved according to the present disclosure by combining anti-Aβ immunotherapy and a curcumin analog, TML-6.

The present disclosure is to provide a method for preventing, ameliorating and/or treating Alzheimer's disease in a subject in need of such treatment, wherein the method comprises administrating to said subject a pharmaceutical combination comprising an effective amount of TML-6, or a pharmaceutically acceptable salt, solvate, hydrate, isotopologue, or prodrug of TML-6 and an effective amount of an anti-Aβ antibody (ab) or an antigen-binding fragment thereof and optionally a pharmaceutically acceptable carrier or excipient,

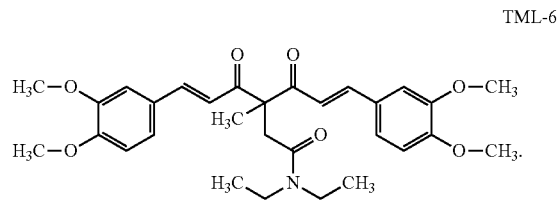 [SMILES: CCN(CC)C(=O)CC(C)(C(=O)/C=C/c1ccc(OC)c(OC)c1)C(=O)/C=C/c1ccc(OC)c(OC)c1]

TML-6

In some embodiments of the disclosure, the TML-6, or the pharmaceutically acceptable salt, solvate, hydrate, isotopologue, or prodrug of TML-6 and the anti-Aβ antibody are co-administered simultaneously, separately or sequentially, or co-administered in combination as a coformulation. In one preferred embodiment of the disclosure, the TML-6, or the pharmaceutically acceptable salt, solvate, hydrate, isotopologue, or prodrug of TML-6 is administered through oral route.

In one embodiment of the disclosure, the anti-Aβ antibody is aducanumab or donanemab.

In some embodiments of the disclosure, the anti-Aβ antibody specifically binds to $A\beta_{1-42}$ or an N-terminal modified form of $A\beta_{1-42}$. In some embodiments of the disclosure, the N-terminal modified $A\beta_{1-42}$ is pyro-glutamate Aβ (pE-$A\beta_{3-42}$). In one embodiment of the disclosure, the anti-Aβ antibody comprises a light-chain CDR1 (L-CDR1) having the sequence of SEQ ID NO: 1, SEQ ID NO: 7, or SEQ ID NO: 14; a light-chain CDR2 (L-CDR2) having the sequence of SEQ ID NO: 2 or SEQ ID NO: 15; a light-chain CDR3 (L-CDR3) having the sequence of SEQ ID NO: 3, SEQ ID NO: 8, SEQ ID NO: 21, or SEQ ID NO: 24; a heavy-chain CDR1 (H-CDR1) having the sequence of SEQ ID NO: 4, SEQ ID NO: 9, SEQ ID NO: 11, SEQ ID NO: 16, or SEQ ID NO: 25; a heavy-chain CDR2 (H-CDR2) having the sequence of SEQ ID NO: 5, SEQ ID NO: 12, SEQ ID NO: 17, SEQ ID NO: 19, SEQ ID NO: 22, or SEQ ID NO: 26; and a heavy-chain CDR3 (H-CDR3) having the sequence of SEQ ID NO: 6, SEQ ID NO: 10, SEQ ID NO: 13, SEQ ID NO: 18, SEQ ID NO: 20, SEQ ID NO: 23, or SEQ ID NO: 27.

Examples of the anti-Aβ antibody include but are not limited to:
an anti-Aβ antibody comprises an H-CDR1 having the sequence of SEQ ID NO: 16, an H-CDR2 having the sequence of SEQ ID NO: 19, an H-CDR3 having the sequence of SEQ ID NO: 20, an L-CDR1 having the sequence of SEQ ID NO: 14, an L-CDR2 having the sequence of SEQ ID NO: 15, and an L-CDR3 having the sequence of SEQ ID NO: 3, named NP106;

an anti-Aβ antibody comprises an H-CDR1 having the sequence of SEQ ID NO: 4, an H-CDR2 having the sequence of SEQ ID NO: 5, an H-CDR3 having the sequence of SEQ ID NO: 6, an L-CDR1 having the sequence of SEQ ID NO: 1, an L-CDR2 having the sequence of SEQ ID NO: 2, and an L-CDR3 having the sequence of SEQ ID NO: 3;

an anti-Aβ antibody comprises an H-CDR1 having the sequence of SEQ ID NO: 9, an H-CDR2 having the sequence of SEQ ID NO: 5, an H-CDR3 having the sequence of SEQ ID NO: 10, an L-CDR1 having the sequence of SEQ ID NO: 7, an L-CDR2 having the sequence of SEQ ID NO: 2, and an L-CDR3 having the sequence of SEQ ID NO: 8;

an anti-Aβ antibody comprises an H-CDR1 having the sequence of SEQ ID NO: 11, an H-CDR2 having the sequence of SEQ ID NO: 12, an H-CDR3 having the sequence of SEQ ID NO: 13, an L-CDR1 having the sequence of SEQ ID NO: 7, an L-CDR2 having the sequence of SEQ ID NO: 2, and an L-CDR3 having the sequence of SEQ ID NO: 3;

an anti-Aβ antibody comprises an H-CDR1 having the sequence of SEQ ID NO: 16, an H-CDR2 having the sequence of SEQ ID NO: 17, an H-CDR3 having the sequence of SEQ ID NO: 18, an L-CDR1 having the sequence of SEQ ID NO: 14, an L-CDR2 having the sequence of SEQ ID NO: 15, and an L-CDR3 having the sequence of SEQ ID NO: 3;

an anti-Aβ antibody comprises an H-CDR1 having the sequence of SEQ ID NO: 9, an H-CDR2 having the sequence of SEQ ID NO: 22, an H-CDR3 having the sequence of SEQ ID NO: 23, an L-CDR1 having the sequence of SEQ ID NO: 7, an L-CDR2 having the sequence of SEQ ID NO: 2, and an L-CDR3 having the sequence of SEQ ID NO: 21; or an anti-Aβ antibody comprises an H-CDR1 having the sequence of SEQ ID NO: 25, an H-CDR2 having the sequence of SEQ ID NO: 26, an H-CDR3 having the sequence of SEQ ID NO: 27, an L-CDR1 having the sequence of SEQ ID NO: 7, an L-CDR2 having the sequence of SEQ ID NO: 2, and an L-CDR3 having the sequence of SEQ ID NO: 24.

In some embodiments of the disclosure, the anti-Aβ antibody is a monoclonal antibody, chimeric antibody, humanized antibody, or human antibody.

Certain embodiments of the effective amount of effective amount of the TML-6 of the present disclosure are those ranging from about 1 mg/kg to 1,000 mg/kg, 5 mg/kg to 900 mg/kg, 5 mg/kg to 800 mg/kg, 10 mg/kg to 700 mg/kg, 20 mg/kg to 600 mg/kg, 30 mg/kg to 500 mg/kg, 40 mg/kg to 400 mg/kg, 50 mg/kg to 300 mg/kg, 60 mg/kg to 200 mg/kg, 70 mg/kg to 150 mg/kg, 80 mg/kg to 120 mg/kg, or 90 mg/kg to 110 mg/kg.

Certain embodiments of the effective amount of effective amount of the anti-Aβ antibody of the present disclosure are those ranging from about 0.1 mg/kg to 800 mg/kg, 0.5 mg/kg to 600 mg/kg, 0.8 mg/kg to 500 mg/kg, 1 mg/kg to 400 mg/kg, 2 mg/kg to 300 mg/kg, 5 mg/kg to 200 mg/kg, 10 mg/kg to 100 mg/kg, 15 mg/kg to 80 mg/kg, 20 mg/kg to 60 mg/kg, 25 mg/kg to 50 mg/kg.

In one embodiment of the disclosure, the method is for synergistically increasing microglial Aβ phagocytosis.

In one embodiment of the disclosure, the method is for promoting microglial ramification around Aβ plaques.

In one embodiment of the disclosure, the method is for reducing Aβ levels in the brain of the subject.

In one embodiment of the disclosure, the method is for treating behavioral abnormality.

In one embodiment of the disclosure, the method is for aberrant gut microbiota of the subject.

The present disclosure also provides a method for reducing a dosage or dose frequency or side effect of a drug for treating Alzheimer's disease in a subject in need of such treatment, wherein the method comprises administrating to said subject an effective amount of TML-6, or a pharmaceutically acceptable salt, solvate, hydrate, isotopologue, or prodrug of TML-6 and optionally a pharmaceutically acceptable carrier or excipient.

In one embodiment of the disclosure, the drug for treating Alzheimer's disease comprises an effective amount of an anti-Aβ antibody or an antigen-binding fragment thereof.

In one embodiment of the disclosure, the side effect comprises amyloid-related imaging abnormalities.

The present disclosure is described in detail in the following sections. Other characteristics, purposes and advantages of the present disclosure can be found in the detailed description and claims.

BRIEF DESCRIPTION OF THE DRAWINGS

FIGS. 1A to 1D show the characteristics of NP106, an anti-Aβ antibody derived from mouse monoclonal hybridoma. FIG. 1A, NP106 binds strongly to oligomeric and aggregated Aβ, and to a lesser extent to pE-Aβ. FIG. 1B, the binding affinity to Aβ was further examined by SPR. FIG. 1C, the response curve to aggregated Aβ is presented. FIG. 1D, confocal imaging also indicates that NP106 detects the deposition of Aβ plaques (in green) in the brain of APP/PS1 mice.

FIGS. 2A to 2G show combination treatment using low-dose NP106 and oral administration of TML-6 outperformed either alone in the reduction of Aβ plaques in APP/PS1 mice. FIG. 2A, Aβ plaque deposition shown by Amylo-glo staining with fluorescent images was reduced by either TML-6 or NP106, while a further reduction was found in mice with combination treatment. Quantification of % of Aβ plaque area (FIG. 2B), number of Aβ plaques (FIG. 2C), area of Aβ plaque size larger than 500 μm$^2$ (FIG. 2D), area of Aβ plaque size smaller than 500 μm$^2$ (FIG. 2E), number of Aβ plaque size larger than 500 μm$^2$ (FIG. 2F), and number of Aβ plaque size smaller than 500 μm$^2$ (FIG. 2G) per section of brain are presented. Data are shown as mean±SEM. *$p<0.05$; $p<0.01$; *$p<0.001$ compared with APP/PS1 controls. #$p<0.05$ compared with the APP/PS1 mice with combination treatment. One-way ANOVA adjusted with Tukey's multiple comparison was used.

FIGS. 3A to 3F show that treatment effects of combination treatment on the reduction of $A\beta_{1-42}$ and $A\beta_{1-40}$ were superior to those by TML-6 or NP106 alone. From all mice used in this study, cerebral $A\beta_{1-42}$ at the levels of total (FIG. 3A) and SDS-insoluble forms (FIG. 3B) were significantly reduced by all treatments, while SDS-soluble forms (FIG. 3C) were slightly reduced. Similarly, $A\beta_{1-40}$ at the levels of total (FIG. 3D) and SDS-insoluble forms (FIG. 3E) were significantly reduced, while SDS-soluble forms (FIG. 3F) were unchanged. Data are shown as mean±SEM. *$p<0.05$; $p<0.01$; *$p<0.001$ compared with APP/PS1 controls. #$p<0.05$; ###$p<0.001$ compared with the APP/PS1 mice with combination treatment. One-way ANOVA adjusted with Tukey's multiple comparison was used.

PS1. FIG. 4A, two-way ANOVA shows that the treatment using NP106 or TML-6 alone demonstrated significant improvements of nesting scores at indicated time points, while a further improvement was found in APP/PS1 mice with combination treatment. FIG. 4B, the superior effectiveness of combination treatment on the recovery of nesting ability was further supported by the analyses of linear regression showing that the significant difference of the slopes of nesting scores between APP/PS1 controls and wt mice ($p<0.01$) was completely abolished by combination treatment ($p<0.01$), but not by TML-6 ($p=0.07173$) or NP106 alone ($p=0.09613$). FIG. 4C, nesting scores were negatively correlated with % of Aβ plaques ($r=-0.431$, $p<0.01$), number of Aβ plaques ($r=-0.4783$, $p<0.01$), and levels of insoluble A$\beta_{1-42}$ ($r=-0.5682$, $p<0.001$). Spearman correlations and the analyses of linear regression with 95% CI (dash-lines in corresponding colors) were tested and significance was set at $p<0.05$.

FIG. 5A, co-localization of the immunoreactivity of Iba1, a microglial marker, and Aβ plaques in the brain of APP/PS1 mice was significantly elevated in combination treatment group, but not in either alone. FIG. 5B, representative skeletonized images from further morphological analyses of microglia were presented. Quantification of morphological analyses indicate that the number of branches (FIG. 5C) and process length (FIGS. 5D-5F) of microglia were synergistically increased by combination treatment. FIG. 5G, total outgrowth as measured by total length of cell-associated skeletonized outgrowth corrected for diagonal lengths was increased by TML-6 alone and combination treatment. FIG. 5H, the number of process was comparable among all groups. FIG. 5I, the cell body size of combination treatment group tended to be smaller than the other groups, albeit not significant. Data are shown as mean±SEM. *$p<0.05$; **$p<0.01$ compared with APP/PS1 controls. One-way ANOVA adjusted with Tukey's multiple comparison was used.

FIG. 6A, a cluster heat map of the thirty-five most abundance at genus level is presented. The abscissa of the cluster heat map denotes the five groups, and the right ordinate denotes bacteria genera. The left is the genera cluster tree, and the phylum is marked in color block. The corresponding value legend of the heat map is the z-score obtained by normalizing the abundance of each genus in all groups. FIG. 6B, analyses of unweighted uniFrac show the significant structural differences of bacterial communities between APP/PS1 controls and wt can be abrogated by all treatments, while APP/PS1 mice with either NP106 or combination treatment were highly significantly different from APP/PS1 controls. FIG. 6C, PCoA of gut bacteria further indicate that the bacterial communities of APP/PS1 mice were different from those of wt and APP/PS1 mice with all treatments, while APP/PS1 mice treated with combination treatment were more similar to those of wt than other treatment groups. *$p<0.05$; ***$p<0.001$. One-way ANOVA adjusted with Tukey's multiple comparison was used.

DETAILED DESCRIPTION OF THE DISCLOSURE

Figure 2D:
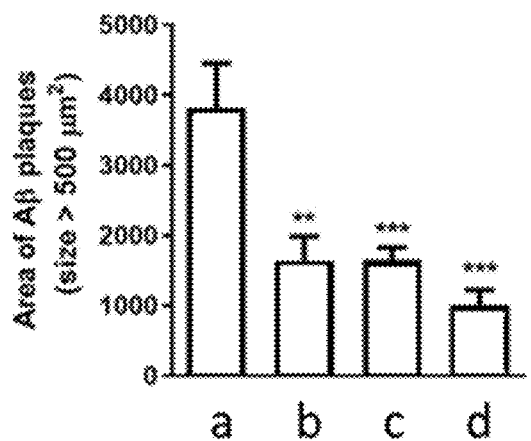

The present disclosure is to provide a method for preventing, ameliorating and/or treating Alzheimer's disease in a subject in need of such treatment, wherein the method comprises administrating to said subject a pharmaceutical combination comprising an effective amount of TML-6, or a pharmaceutically acceptable salt, solvate, hydrate, isotopologue, or prodrug of TML-6 and an effective amount of an anti-A beta antibody or an antigen-binding fragment thereof and optionally a pharmaceutically acceptable carrier or excipient,

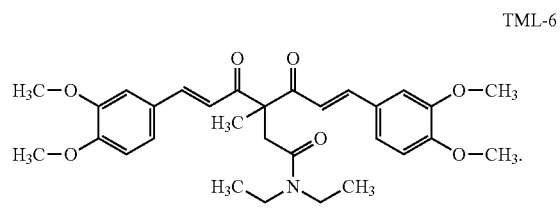 [SMILES: CCN(CC)C(=O)CC(C)(C(=O)/C=C/c1ccc(OC)c(OC)c1)C(=O)/C=C/c1ccc(OC)c(OC)c1]

The present disclosure can be more readily understood by reference to the following detailed description of various embodiments of the disclosure, the examples, and the chemical drawings and tables with their relevant descriptions. It is to be understood that unless otherwise specifically indicated by the claims, the disclosure is not limited to specific preparation methods, carriers or formulations, or to particular modes of formulating the compounds of the disclosure into products or compositions intended for topical, oral or parenteral administration, because as one of ordinary skill in the relevant arts is well aware, such things can, of course, vary. It is also to be understood that the terminology used herein is for the purpose of describing particular embodiments only and is not intended to be limiting.

As utilized in accordance with the present disclosure, the following terms, unless otherwise indicated, shall be understood to have the following meaning:

As used herein, the use of "or" means "and/or" unless stated otherwise. In the context of a multiple dependent claim, the use of "or" refers back to more than one preceding independent or dependent claim in the alternative only.

The term "a pharmaceutically acceptable analog" or "pharmaceutically acceptable analogs" as used herein denotes a compound that is modified from the compound of the disclosure but has properties and efficacies that are the same as or better than those of the compound of the disclosure. In some embodiments, the pharmaceutically acceptable analog is a pharmaceutically acceptable salt, solvate, hydrate, isotopologue, or prodrug of the compound of the disclosure.

TML-6 of the disclosure can also exist as a solvate or hydrate. Thus, these compounds may crystallize with, for example, waters of hydration, or one, a number of, or any fraction of molecules of the mother liquor solvent. The solvates and hydrates of such compounds are included within the scope of this disclosure.

"Optional" or "optionally" means that the subsequently described event or circumstance may or may not occur, and that the description includes instances where said event or circumstance occurs and instances where it does not. For example, the phrase "optionally comprising an agent" means that the agent may or may not exist.

It must be noted that, as used in the specification and the appended claims, the singular forms "a," "an" and "the" include plural referents unless the context clearly dictates otherwise. Thus, unless otherwise required by context, singular terms shall include the plural and plural terms shall include the singular.

The term "subject" as used herein denotes any animal, preferably a mammal, and more preferably a human. Examples of subjects include humans, non-human primates, rodents, guinea pigs, rabbits, sheep, pigs, goats, cows, horses, dogs and cats.

The term "effective amount" of an active ingredient as provided herein means a sufficient amount of the ingredient to provide the desired regulation of a desired function. As will be pointed out below, the exact amount required will vary from subject to subject, depending on the disease state, physical conditions, age, sex, species and weight of the subject, the specific identity and formulation of the composition, etc. Dosage regimens may be adjusted to induce the optimum therapeutic response. For example, several divided doses may be administered daily or the dose may be proportionally reduced as indicated by the exigencies of the therapeutic situation. Thus, it is not possible to specify an exact "effective amount." However, an appropriate effective amount can be determined by one of ordinary skill in the art using only routine experimentation.

The term "preventing" or "prevention" is recognized in the art, and when used in relation to a condition, it includes administering, prior to onset of the condition, an agent to reduce the frequency or severity of or delay the onset of symptoms of a medical condition in a subject relative to a subject which does not receive the agent.

The terms "treatment," "treating," and "treat" generally refer to obtaining a desired pharmacological and/or physiological effect. The effect maybe preventive in terms of completely or partially preventing a disease, disorder, or symptom thereof, and may be therapeutic in terms of a partial or complete cure for a disease, disorder, and/or symptoms attributed thereto. "Treatment" used herein covers any treatment of a disease in a mammal, preferably a human, and includes (1) suppressing development of a disease, disorder, or symptom thereof in a subject or (2) relieving or ameliorating the disease, disorder, or symptom thereof in a subject.

As used herein, an "antibody" and "antigen-binding fragments thereof" encompass naturally occurring immunoglobulins (e.g., IgM, IgG, IgD, IgA, IgE, etc.) as well as non-naturally occurring immunoglobulins, including, for example, single chain antibodies, chimeric antibodies (e.g., humanized murine antibodies), heteroconjugate antibodies (e.g., bispecific antibodies), Fab', F(ab')$_2$, Fab, Fv, and rIgG. As used herein, an "antigen-binding fragment" is a portion of the full-length antibody that retains the ability to specifically recognize the antigen, as well as various combinations of such portions.

As used herein, the term "immunotherapy" refers to the treatment of a subject afflicted with, or at risk of contracting or suffering a recurrence of a disease by a method comprising inducing, enhancing, suppressing or otherwise modifying an immune response.

The pharmaceutical combination of the present disclosure may be formulated with a "carrier." As used herein, "carrier" includes any solvent, dispersion medium, vehicle, coating, diluent, antibacterial, and/or antifungal agent, isotonic agent, absorption delaying agent, buffer, carrier solution, suspension, colloid, and the like. The use of such media and/or agents for pharmaceutical active substances is well known in the art. For example, the pharmaceutical combinations can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, lotion, gel, ointment, or a controlled-release patch or spray applied to the skin; (4) intravaginally or intrarectally, for example, as a pessary, cream, suppository or foam; (5) sublingually; (6) ocularly; (7) transdermally; (8) transmucosally; or (9) nasally.

As used herein, the term "combination", "therapeutic combination" or "pharmaceutical combination", as used herein, defines either a fixed combination in one dosage unit form or a kit of parts for the combined administration where Compound A and Compound B may be administered independently at the same time or separately within time intervals.

As used herein, the term "pharmaceutically acceptable" is defined herein to refer to those compounds, materials, compositions and/or dosage forms, which are, within the scope of sound medical judgment, suitable for contact with the tissues a subject, e.g., a mammal or human, without excessive toxicity, irritation allergic response and other problem complications commensurate with a reasonable benefit/risk ratio.

As used herein, the term "co-administration" or "combined administration" as used herein is defined to encompass the administration of the selected therapeutic agents to a single patient, and are intended to include treatment regimens in which the agents are not necessarily administered by the same route of administration or at the same time.

According to the disclosure, TML-6, a synthetic curcumin analog, which possesses anti-inflammatory properties involved in multiple mechanisms in AD pathogenesis, reveals a significantly better activity than curcumin in reducing brain Aβ level and anti-inflammation than curcumin, testifying the superior bioavailability of the curcumin analog TML-6 to traditional curcumin.

In one embodiment of the disclosure, the anti-Aβ antibody in both mouse and fully humanized versions is provided, which recognizes various Aβ species and N-terminally modified pyro-glutamate Aβ. This antibody exerts multifaceted functionality in the recovery of neuroplasticity and the transformation of over-activated microglia into ramified microglia, while enhancing microglial Aβ phagocytosis in vitro and in vivo.

In one embodiment of the disclosure, the anti-Aβ antibody is aducanumab or donanemab.

In some embodiments of the disclosure, the anti-Aβ antibody specifically binds to Aβ$_{1-42}$ or an N-terminal modified form of Aβ$_{1-42}$. In some embodiments, the N-terminal modified Aβ$_{1-42}$ is pyro-glutamate Aβ (pE-Aβ$_{3-42}$). In some embodiments of the disclosure, the anti-Aβ antibody comprises an L-CDR1 having the sequence of SEQ ID NO: 1, SEQ ID NO: 7, or SEQ ID NO: 14; an L-CDR2 having the sequence of SEQ ID NO: 2 or SEQ ID NO: 15; an L-CDR3 having the sequence of SEQ ID NO: 3, SEQ ID NO: 8, SEQ ID NO: 21, or SEQ ID NO: 24; an H-CDR1 having the sequence of SEQ ID NO: 4, SEQ ID NO: 9, SEQ ID NO: 11, SEQ ID NO: 16, or SEQ ID NO: 25; an H-CDR2 having the sequence of SEQ ID NO: 5, SEQ ID NO: 12, SEQ ID NO: 17, SEQ ID NO: 19, SEQ ID NO: 22, or SEQ ID NO: 26; and an H-CDR3 having the sequence of SEQ ID NO: 6, SEQ ID NO: 10, SEQ ID NO: 13, SEQ ID NO: 18, SEQ ID NO: 20, SEQ ID NO: 23, or SEQ ID NO: 27.

Examples of the anti-Aβ antibody include but are not limited to:

an anti-Aβ antibody comprises an H-CDR1 having the sequence of SEQ ID NO: 16, an H-CDR2 having the sequence of SEQ ID NO: 19, an H-CDR3 having the sequence of SEQ ID NO: 20, an L-CDR1 having the sequence of SEQ ID NO: 14, an L-CDR2 having the sequence of SEQ ID NO: 15, and an L-CDR3 having the sequence of SEQ ID NO: 3, named NP106;

an anti-Aβ antibody comprises an H-CDR1 having the sequence of SEQ ID NO: 4, an H-CDR2 having the sequence of SEQ ID NO: 5, an H-CDR3 having the sequence of SEQ ID NO: 6, an L-CDR1 having the sequence of SEQ ID NO: 1, an L-CDR2 having the sequence of SEQ ID NO: 2, and an L-CDR3 having the sequence of SEQ ID NO: 3;

an anti-Aβ antibody comprises an H-CDR1 having the sequence of SEQ ID NO: 9, an H-CDR2 having the sequence of SEQ ID NO: 5, an H-CDR3 having the sequence of SEQ ID NO: 10, an L-CDR1 having the sequence of SEQ ID NO: 7, an L-CDR2 having the sequence of SEQ ID NO: 2, and an L-CDR3 having the sequence of SEQ ID NO: 8;

an anti-Aβ antibody comprises an H-CDR1 having the sequence of SEQ ID NO: 11, an H-CDR2 having the sequence of SEQ ID NO: 12, an H-CDR3 having the sequence of SEQ ID NO: 13, an L-CDR1 having the sequence of SEQ ID NO: 7, an L-CDR2 having the sequence of SEQ ID NO: 2, and an L-CDR3 having the sequence of SEQ ID NO: 3;

an anti-Aβ antibody comprises an H-CDR1 having the sequence of SEQ ID NO: 16, an H-CDR2 having the sequence of SEQ ID NO: 17, an H-CDR3 having the sequence of SEQ ID NO: 18, an L-CDR1 having the sequence of SEQ ID NO: 14, an L-CDR2 having the sequence of SEQ ID NO: 15, and an L-CDR3 having the sequence of SEQ ID NO: 3;

an anti-Aβ antibody comprises an H-CDR1 having the sequence of SEQ ID NO: 9, an H-CDR2 having the sequence of SEQ ID NO: 22, an H-CDR3 having the sequence of SEQ ID NO: 23, an L-CDR1 having the sequence of SEQ ID NO: 7, an L-CDR2 having the sequence of SEQ ID NO: 2, and an L-CDR3 having the sequence of SEQ ID NO: 21; or an anti-Aβ antibody comprises an H-CDR1 having the sequence of SEQ ID NO: 25, an H-CDR2 having the sequence of SEQ ID NO: 26, an H-CDR3 having the sequence of SEQ ID NO: 27, an L-CDR1 having the sequence of SEQ ID NO: 7, an L-CDR2 having the sequence of SEQ ID NO: 2, and an L-CDR3 having the sequence of SEQ ID NO: 24.

```
                                              SEQ ID NO: 1
Cys Arg Ser Ser Gln Thr Ile Val His Ser Asn Gly Asn
Thr Tyr Leu Glu

SEQ ID NO: 2
Lys Val Ser Asn Arg Phe Ser

SEQ ID NO: 3
Phe Gln Gly Ser His Val Pro Leu Thr

SEQ ID NO: 4
Thr Ser Gly Met Asn Val Gly

SEQ ID NO: 5
His Ile Trp Trp Asp Asp Lys Tyr Tyr Asn Pro Ser
Leu Lys Ser

SEQ ID NO: 6
Arg Arg Ser Ile Arg Gly Ser Asp Tyr Phe Asp Tyr

SEQ ID NO: 7
Cys Arg Ser Ser Gln Ser Ile Val His Ser Asn Gly Asn
Thr Tyr Leu Glu

SEQ ID NO: 8
Phe Gln Gly Ser Leu Val Pro Leu Thr

SEQ ID NO: 9
Thr Ser Gly Met Gly Val Gly

SEQ ID NO: 10
Arg Arg Ala Leu Arg Asn Val Val Ala Asp Ala Met Asp
Tyr

SEQ ID NO: 11
Thr Ser Ala Val Gly Val Ser

SEQ ID NO: 12
His Ile Tyr Trp Asp Asp Lys Arg Tyr Asn Pro Ser
Leu Lys Ser

SEQ ID NO: 13
Arg Arg Pro Tyr Tyr Arg Tyr Asp Val Asp Ala Met Asp
Tyr

SEQ ID NO: 14
Cys Arg Ser Ser Gln Asn Ile Val His Ser Asn Gly Asn
Thr Tyr Leu Glu

SEQ ID NO: 15
Thr Val Ser Asn Arg Phe Ser

SEQ ID NO: 16
Ser Ser Val Leu Gly Val Ser

SEQ ID NO: 17
His Ile Tyr Trp Asp Asp Arg Arg Tyr Asn Pro Ser
Leu Lys Ser

SEQ ID NO: 18
Arg Arg Gly Lys Met Gly Arg Gly Leu Asp Ala Met Asp
Tyr
```

-continued

SEQ ID NO: 19
His Ile Tyr Trp Asp Asp Asp Arg Arg Tyr Asn Pro Ser
Leu Arg Ser

SEQ ID NO: 20
Arg Arg Gly Lys Met Gly Arg Gly Leu Asp Ala Leu Asp
Phe

SEQ ID NO: 21
Phe Gln Gly Ser Arg Val Pro Leu Thr

SEQ ID NO: 22
His Ile Trp Trp Asp Asp Asp Lys Tyr Phe Asn Pro Ser
Leu Lys Ser

SEQ ID NO: 23
Arg Arg Ser Leu Lys Trp Leu Asp Ala Met Asp Tyr

SEQ ID NO: 24
Phe Gln Ser Ser Arg Val Pro Leu Thr

SEQ ID NO: 25
Thr Ser Gly Met Gly Val Ser

SEQ ID NO: 26
His Ile Tyr Trp Asp Asp Asp Lys Ser Tyr Asn Pro Ser
Leu Lys Ser

SEQ ID NO: 27
Arg Arg Arg Asn Trp Val Ile Thr Asp Ala Met Glu Tyr

In clinical trials, passive immunotherapy using antibodies against Aβ, such as Biogen's aducanumab, has been shown to be the most promising agent to reduce Aβ accumulation as well as tauopathy in AD patients (Cummings J, et al. AD drug development pipeline: 2018. Alzheimer's Dement (NY). 2018; 4:195-214; Geerts et al., Alzheimers Dement. 2020 June; 16(6):862-872), while higher dosing of anti-Aβ antibody is limited by increased risk of adverse effect of amyloid-related imaging abnormalities (ARIA), especially in AD patients with apolipoprotein E (APOE) ε4 allele (VandeVrede et al., Alzheimers Dement (Amst). 2020 Oct. 9; 12(1):e12101). The underlying mechanisms of aducanumab's beneficial effects involve antibody-induced microglia-mediated Aβ clearance. However, the treatment efficacy of aducanumab on the cognitive improvement by the immunotherapy in phase III clinical trials remains debatable (Fillit et al., Nat Rev Neurol. 2021 Jan. 13. doi: 10.1038/s41582-020-00454-9). AD pathologies in the brain have been proposed to occur up to 20 years before the onset of clinical manifestations in AD (Jack et al., Alzheimers Dement. 2018 April; 14(4):535-562). By the time when AD is diagnosed, the progression of the disease is too complex to be managed. The severely compromised functioning of the brain due to chronic pathological insults makes AD treatment more difficult, and a multi-target, rather than a single-target, treatment regimen is required for this complex disease. Therefore, this may explain at least in part why the single-target immunotherapy has an uncertain effectiveness in treating AD (Knopman et al., Alzheimers Dement. 2020. doi: 10.1002/alz.12213). A favorable combination of diminished microglia-mediated neuro-inflammation and enhanced AP clearance has been proposed as a promising therapeutic paradigm.

In some embodiments, the pharmaceutical combination of the disclosure may be provided in a single formulation or medicament. In other embodiments, the pharmaceutical combination of the disclosure may be provided in separates formulations or medicaments. A pharmaceutical combination may be formulated in a variety of and/or a plurality of forms adapted to one or more preferred routes of administration. Thus, a pharmaceutical combination can be administered via one or more known routes including, for example, oral, parenteral (e.g., intradermal, transcutaneous, subcutaneous, intramuscular, intravenous, intraperitoneal, etc.), or topical (e.g., intranasal, intrapulmonary, intramammary, intravaginal, intrauterine, intradermal, transcutaneous, rectally, etc.). A pharmaceutical combination, or a portion thereof, can be administered to a mucosal surface, such as by administration to, for example, the nasal or respiratory mucosa (e.g., by spray or aerosol). A pharmaceutical combination, or a portion thereof, also can be administered via a sustained or delayed release.

A formulation may be conveniently presented in unit dosage form and may be prepared by methods well known in the art of pharmacy. Methods of preparing a combination with a pharmaceutically acceptable carrier include the step of bringing the pharmaceutical combination of the disclosure into association with a carrier that constitutes one or more accessory ingredients. In general, a formulation may be prepared by uniformly and/or intimately bringing the active compound into association with a liquid carrier, a finely divided solid carrier, or both, and then if necessary, shaping the product into the desired formulations.

To achieve such a multi-targeting therapy with minimal use of targeted drugs, a combination therapy is disclosed in the disclosure for treating APP/PS1 mice using a low-dose anti-Aβ antibody in combination with TML-6 through oral route to avoid the potential stresses from long-term oral gavage. The synergistic effects of combination treatment are addressed in this disclosure.

In one embodiment of the disclosure, the method is for synergistically increasing microglial Aβ phagocytosis and/ or for promoting microglial ramification around Aβ plaques and/or for reducing Aβ levels in the brain of the subject and/or for treating behavioral abnormality.

According to the disclosure, combining anti-Aβ antibody and TML-6, but not either alone, synergistically increased microglial Aβ phagocytosis, while promoting microglial ramification around Aβ plaques and a further reduction of Aβ levels in the brain. In an animal model of the present disclosure, abnormal nesting ability in APP/PS1 mice was completely restored to wild-type (wt) levels when combined with anti-Aβ antibody and TML-6, and nesting scores are negatively correlated to cerebral Aβ loads.

In one embodiment of the disclosure, the method is for aberrant gut microbiota of the subject. It has been recently recognized that gut microbiota may influence brain functioning and contributes to the pathogenesis of AD, while composition of gut microbiota is altered in AD and with aging (Claesson et al., Nature. 2012 Aug. 9; 488(7410):178-84; Vogt et al., Sci Rep. 2017 Oct. 19; 7(1):13537). Although this bidirectional gut-brain axis is not fully understood, increasing lines of evidence from animal studies demonstrate that the interactions between gut microbiota and AD pathology can be mediated by neural, endocrine and immune signals (Carabotti et al., Ann Gastroenterol. 2015 April-June; 28(2):203-209). Intriguingly, gut microbiota affects microglial functions and regulates their gene expressions in response to pathological conditions (Erny et al., Nat. Neurosci. 2015 July; 18(7):965-977; Matcovitch-Natan et al., Science 2016 Aug. 19; 353(6301):aad8670). Short chain fatty acids (SCFAs), comprised mostly of acetate, propionate and butyrate, derived from bacterial metabolites were identified as signaling molecules, while the mechanisms underlying these neuroactive effects of SCFAs on microglial functions and neuro-immunoendocrine regulation remain largely unknown (Erny et al., Nat. Neurosci. 2015 July; 18(7):965-977; Silva et al., Front Endocrinol (Lausanne). 2020; 11: 25). Of note, a butyrate-producing bacteria was found to be reduced in AD patients (Ling et al., Front Cell Dev Biol. 2021 Feb. 4; 8:634069), and treatments with a butyrate-producing bacteria were reported to be beneficial against AD-like pathology and be able to prevent behavioral deficits in mice (Sun et al., Mol Nutr Food Res. 2020 January; 64(2):e1900636). In an animal model of the disclosure, intriguingly, data from microbiome show that the aberrant gut microbiota in APP/PS1 mice was normalized by combination treatment to the levels resembling wt littermates. Furthermore, linear discriminant analyses identify seven bacteria genera that were highly correlated with both nesting performance and $A\beta$ pathology in APP/PS1 mice.

Combination treatment using low-dose anti-$A\beta$ antibody and oral administration of TML-6 reduced many indications of $A\beta$ pathology and improved behavioral deficits in APP/PS1 mice, which was superior to either alone. Importantly, these data imply a potential clinical significance for AD therapy suggesting that the therapeutic effectiveness of anti-$A\beta$ antibody drug can be synergistically enhanced by combining TML-6 through food intake. Furthermore, it is pivotal that reducing the dosage of anti-$A\beta$ antibody drug, while maintaining the therapeutic efficacy of high dose of antibody drug, is not only more cost-effective in clinical practice, but also minimize the risk of anti-$A\beta$ antibody-related adverse effects caused by high dose of antibody drug. in this disclosure, the beneficial effects of combination treatment on counteracting: D-like pathology in APP/PS1 mice was at least attributed to the rejuvenation of microglia from senescence morphology, leading an enhanced microglia-mediated $A\beta$ clearance. To the best of our knowledge, this is the first study to report the synergistic effects of combination treatment on microglial $A\beta$ phagocytosis along with their morphological changes from de-ramified/over-activated into ramified. Microglia can be rejuvenated by combined the anti-$A\beta$ antibody and TML-6 as evidenced by presenting ramified morphologies resembling to the resting microglia in a healthy brain. These morphological changes into a healthy appearance by combination treatment were in line with the increased $A\beta$ phagocytosis and a robust reduction of $A\beta$ pathology.

The present disclosure also provides a method for reducing a dosage or dose frequency or side effect of a drug for treating Alzheimer's disease in a subject in need of such treatment, wherein the method comprises administrating to said subject an effective amount of TML-6, or a pharmaceutically acceptable salt, solvate, hydrate, isotopologue, or prodrug of TML-6 and optionally a pharmaceutically acceptable carrier or excipient.

In one embodiment of the disclosure, the drug for treating Alzheimer's disease comprises an effective amount of an anti-$A\beta$ antibody or an antigen-binding fragment thereof.

In one embodiment of the disclosure, the side effect comprises amyloid-related imaging abnormalities.

The following examples are provided to aid those skilled in the art in practicing the present disclosure.

EXAMPLES

Methods:
Animals
APP/PS1 (B6.Cg/(APPswe, PSEN1dE9)85Dbo/J) transgenic mice that engineered to develop AD-like pathology APP/PS1 transgenic mice at ages of three months and wild-type (wt) littermates were used for this study. Animals were housed under controlled room temperature (24±1° C.) and humidity (55-65%) with 12:12 h (07:00-19:00) light-dark cycle. Experiments have been performed as approved by the Institutional Animal Care and Use Committees of National Health Research Institutes (NHRI).

Preparation of TML-6 Chow Diet and Estimated Daily Uptake of TML-6

TML-6, a small molecule curcumin analog, was used in this study. A regular rodent chow (Laboratory Rodent Diet 5001) supplemented with TML-6 at 100 mg/kg rodent chow was provided by Merry Life Biomedical company, Ltd. Content, purity, and stability of TML-6 in TML-6 diet at different storage conditions were analyzed using LC/MS/MS via service provided by the Development Center for Biotechnology, Taiwan. TML-6 diet was stored at 4° C. and was added to mouse cages twice a week for ad libitum feeding regimens. Daily uptake of TML-6 in APP/PS1 mice was estimated based on average consumption of rodent chow supplemented with TML-6 at 100 mg/kg chow for 24 hr or 8 days. Briefly, three APP/PS1 mice were housed individually in metabolic cages with an apparatus for measuring food-intake. Estimated TML-6 uptake per kg body weight per day was calculated by multiplying the daily consumption of TML-6 supplemented chow by the amount of TML-6 in the chow divided by body weight.

Combination Treatment Regimen

NP106 is derived from a novel hybridoma monoclonal antibody against human oligomeric $A\beta_{1-42}$ (oA$\beta$), which has been cloned into a murine IgG1 and is routinely produced using pcDNA3.4 expression plasmid in Expi-CHO™ Expression system followed by purification using protein G. The binding epitope of NP106 is estimated to be located at the N-terminal residues 3 to 10 of $A\beta_{1-42}$ as examined by epitope mapping and molecular dynamic modeling, and NP106 at 30 mg/kg significantly reduces $A\beta$ loads in APP/PS1 mice.

For study of combination treatment, APP/PS1 mice were randomly assigned into four groups and were subjected to the treatments at 3 months of age (the early/prodromal stage of AD) for 4 months. Wt littermates (n=10) were also included for behavioral tests as a WT control group at 7 months. Due to the spontaneous death in APP/PS1 mice, APP/PS1 controls (n=9), TML-6 group (n=10), NP106 group (n=11) and NP106 and TML-6 combination group (n=11) were included for pathological and behavioral examinations in this study. APP/PS1 mice were on regular rodent chow plus weekly intraperitoneal injection (i.p.) injection of 0.9% saline (APP/PS1 control group), regular rodent chow with TML-6 plus weekly i.p. injection of 0.9% saline (TML-6 group), regular rodent chow plus weekly i.p. injection of NP106 at 3 mg/kg body weight (NP106 group), or regular rodent chow with TML-6 plus weekly i.p. injection of NP106 at 3 mg/kg body weight (NP106+TML-6 group). Body weight was recorded weekly. After 4 months of treatments, mice at age of 7 months were subjected to the following examinations.

Pathological Examination by Confocal Microscopy

Brain sections were fixed in 4% paraformaldehyde followed by cryoprotection with 30% sucrose in 1×PBS. Floating sections at 30 μm thickness were stored in 1×PBS with 0.05% sodium azide at 4° C. until use. Amylo-Glo RTD™ (TR-400-AG, Biosensis, Thebarton, Australia) was used for detection of amyloid-$\beta$ (A$\beta$) plaques in the brain sections per manufacturer's instruction. The sections were mounted on the slide covered with mounting medium (Vectashield H-1000, Vector Laborotories, Burlingame, Calif., USA). Images were acquired using Leica confocal microscopy imaging system. Numbers of Aβ deposits and fluorescent area positive for AP deposits were normalized with total area of the section using MetaMorph imaging software. Quantification for sizes of AP deposits larger or smaller than 500 µm² were presented. For colocalization, sections were stained with Amylo-Glo followed by 3 hr-incubation of antibody specific for microglia (Iba1, Abcam, Cambridge, CB2 0AX, UK) at 1:100 dilution. Secondary antibody conjugated with Alexa Fluor 488 (Invitrogen) was then used, and the sections mounted on the slide were subjected to analysis using Leica confocal microscopy imaging system.

Measurements of Levels of Aβ Species by ELISA.

Frozen mouse brains were homogenized with a Dounce homogenizer in 1×PBS (20% homogenate). For measuring levels of Aβ in brain homogenates, 8 volumes of cold 5M guanidine-HCl (Sigma, Catalog number: G3272) in 50 mM Tris (J.T. Baker, Catalog number: 4109-02) were added into the homogenate followed by shaking at room temperature for four hours. The samples were then diluted ten-fold with cold PBS containing protease inhibitor cocktail and were subjected to centrifugation at 16,000×g for 20 min at 4° C. The supernatant was used for quantitative analyses of Aβ40 and Aβ42 levels using ELISA kits (Invitrogen-Thermo Fisher Scientific, Aβ40 Catalog number: KHB3481; Aβ42 Catalog number: KHB3441) according to the instructions.

For measuring AP levels at soluble and insoluble forms, 100 µl of 1% SDS (Sigma, Catalog number: L3771) in PBS was added into 100 µl of homogenates followed by ultra-centrifugation at 175×kg for 20 min at 4° C. The resulting supernatant was stored as SDS soluble form of Aβ. The pellet was then dissolved in 3M Guanidine HCl for 4 hr at 4° C. followed by ultracentrifugation at 175×kg for 20 min at 4° C. The supernatant was stored as insoluble form of Aβ. ELISAs were performed according to the manufacturer's instructions. Results were analyzed using an ELISA reader (SpectraMaxM2, Molecular Devices) at a wavelength of 450 nm. The standard curve was established and then used to calculate the level of Aβ42 in the tissues. Values were expressed as pg/mg.

Behavioral Tests

Before the test for nesting, mice were individually housed for 5 hr. A nestlet pressed-cotton square (Ancare) was then placed into each cage 1 hour before the start of the dark cycle. Pictures of a nestlet were taken at indicated time points, and the entire test underwent for 52 hr. Nest construction was scored by two persons unaware of treatments using a 5-point scaling system as described previously (Yeh et al. 2015). Briefly, a score of 1 indicates a >90% intact nestlet, whereas a score of 5 indicates a <10% intact nestlet and the construction of a nest with an obvious crater.

To evaluate spatial learning and memory deficits in APP/PS1 mice, a circular pool of 120 cm in diameter and 40 cm in height was used. The pool was filled with milk at 22-24 ° C. to approximately 20 cm in deep. A hidden platform was submerged 1 cm below the surface of milk. All experimental mice were transferred to the behavior testing room 30 min prior to the water maze to habituate to the test environment. During the training course, mice received 3 trials per day with a 60-minute inter-trial interval for 6 days. Probe test without the hidden platform was performed at day 7 and mice were allowed to investigate for 60 seconds. An overhead camera and a computerized video imaging analysis system were used to analyze the swimming paths and the escape latency.

Gut Microbiota Analysis Using 16 S rDNA Sequencing

Animals were anesthetized followed by fecal bacterial 16S rDNA extraction. Fecal samples (0.2-0.3 g per mouse) were collected from the colon of mice and immediately stored at −80° C. until use. DNA extraction and the following analyses of the gut microbiota were performed by Biotools Microbiome Research Center Co., Ltd, Taiwan. Briefly, DNA extraction was carried out using the QIAamp Fast DNA Stool Kit (QIAGEN, Hilden, Germany) according to manufacturer's instruction. For analysis of the phylogenetic composition of the gut microbiota, the V3-V4 region of the 16S rDNA gene was amplified followed by sequencing using the 16S amplicon sequencing Illumina MiSeq 2500 platform. A beta diversity distance matrix was computed from QIIME version 1.9.0. operational taxonomic unit (OTU) using unweighted UniFrac analysis. Principal component analysis (PCA), partial least squares discriminant analysis (PLS-DA), and a heatmap of RDA-identified key OTUs were used to analyze the beta diversity. The characteristics of the gut microbiota were analyzed by linear discriminant analysis (LDA) effect size (LEfSe) for biomarker discovery. LEfSe detects the features with significant differences in abundance using the Kruskal-Wallis rank sum test and applies LDA to evaluate the effect size of each feature.

Statistics

Version 5.0 of Prism software (Graph Pad Software, Inc., La Jolla, CA, USA) was used for statistical analysis. Significance among groups were analyzed using the one-way or two-way ANOVA followed by Tukey's multiple comparison post-hoc tests, and two-tailed t-tests were used where applicable. Pearson correlations (r) were tested for parametric measurements, and Spearman correlations (ρ) were tested for non-parametric nesting scoring. Analyses of linear regression was tested and significance throughout was set at $p<0.05$.

Example 1 Descriptives of the Combination Treatment Using NP106 and TML-6

Combination treatment was achieved by using passive immunotherapy of a newly developed Aβ antibody, NP106, and TML-6. While TML-6 was reported previously, NP106 binds strongly to oligomeric and aggregated Aβ, and to a lesser extent to pE-Aβ (FIG. 1A). The binding affinity to Aβ was further examined by SPR (FIG. 1B), which response curve to aggregated Aβ is presented (FIG. 1C). Confocal imaging also indicates that NP106 detects the deposition of Aβ plaques in the brain of APP/PS1 mice (FIG. 1D). To investigate the potential effectiveness of combination treatment against AD, a low-dose of NP106 at 3 mg/kg with oral administration of TML-6 was applied to APP/PS1 mice, and mice in four groups, including APP/PS1 controls, NP106 alone, TML-6 supplemented diet alone, and a combination of NP106 and TML-6, were studied. A regular rodent chow was prepared with supplementation of TML-6 at 100 mg/kg chow. To examine the TML-6 content in TML-6 diet, LC/MS/MS analysis was used. Results show that the amount of TML-6 in rodent chow at various storage conditions was stable and the estimated average was 0.795 mg/g chow. Since daily consumption of TML-6 supplemented chow was estimated to be 4.2 g for each mouse with a body weight of approximately 0.03 kg, the average daily consumption of TML-6 was estimated to be 111.3 mg/kg/d. In addition, body weights were recorded weekly throughout the 6-month period of study, which are shown to be comparable among all groups, suggesting that APP/PS1 mice and wt littermates were well-tolerated to the treatments. After 4 months of treatments, APP/PS1 mice were subjected to behavioral tests, including nesting and Morris water maze, followed by pathological examinations for analyses of Aβ pathology in the brain. Fecal microbiome was analyzed by the 16S rRNA sequencing.

Figure 2E:
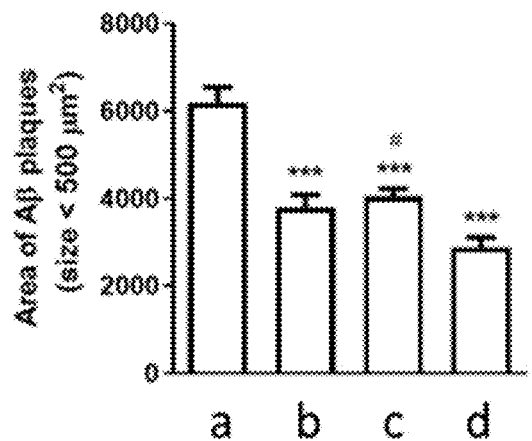
Figure 2F:
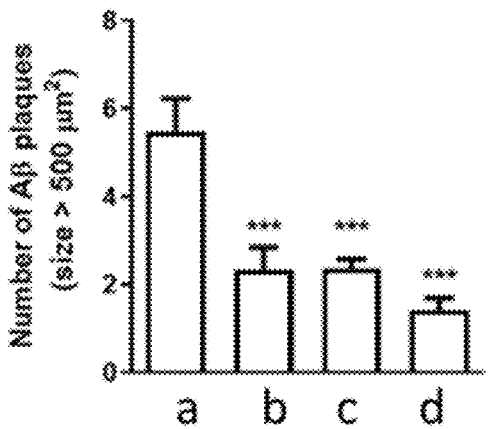
Figure 2G:
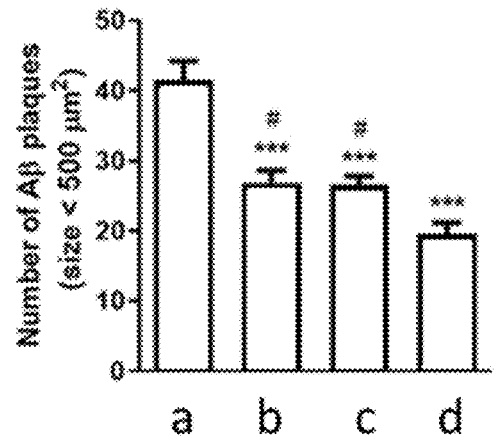

Example 2 The Combination Regimen Prevailed Monotherapies of NP106 or TML-6 Alone in the Reduction of Aβ Pathology Aβ deposition was performed by Amylo-glo staining on brain sections, and levels of $A\beta_{1-40}$ and $A\beta_{1-42}$ in the brain were measured by ELISA. Data from Amylo-glo staining show that Aβ depositions were apparent in both cortex and hippocampus of APP/PS1 mice at age of 7 months as shown in FIG. 2A, while mice with TML-6 or NP106 alone or combination treatment have lower levels of Aβ depositions. Quantification of Aβ depositions indicates that % of Aβ plaques area in the brain was significantly reduced by all treatments, although a slightly lower level was observed in combination treatment group compared to TML-6 or NP106 alone (FIG. 2B) Similar results were found in the number of Aβ plaques, and a further reduction in combination treatment group was found to be significant compared to NP106 alone (FIG. 2C). Further analyses of the treatment effects on different sizes of Aβ plaques show that the area and the number of Aβ plaques in sizes greater or smaller than 500 μm$^2$ were similarly reduced by all treatments (FIGS. 2D-2G). Intriguingly, a better efficacy on reducing Aβ plaques in sizes smaller than 500 μm$^2$ was found by combination treatment (FIGS. 2E, 2G).

Figure 3E:
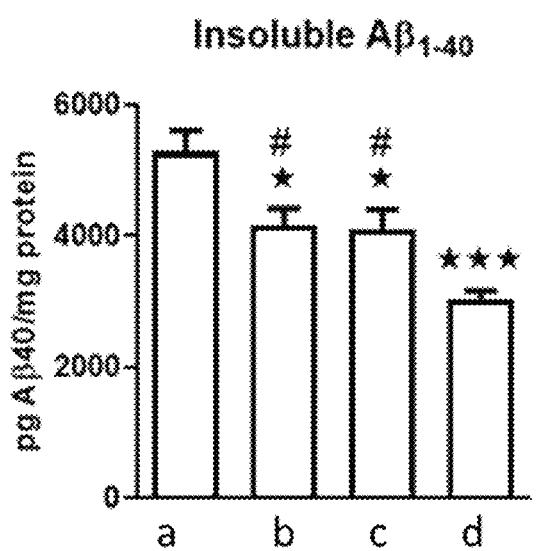
Figure 3F:
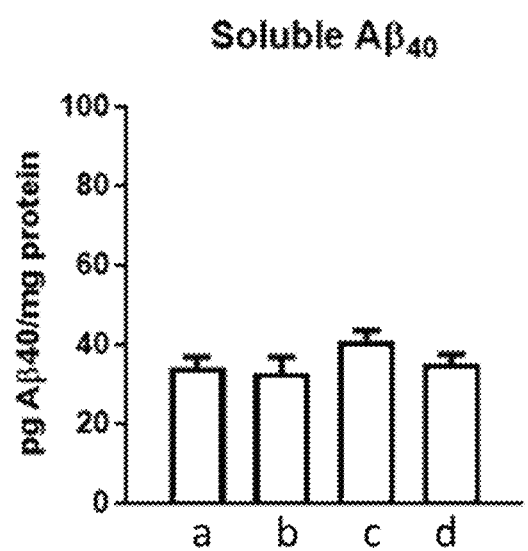

To examine the treatment effects on the levels of Aβ, brain homogenates were subjected to the sample preparations by the aforementioned methods and measured different forms of $A\beta_{1-40}$ and $A\beta_{1-42}$. As shown in FIG. 3A, $A\beta_{1-42}$ in the brain homogenates of APP/PS1 mice was significantly reduced by all treatments, while combination treatment had a highly significant reduction. As expected, insoluble $A\beta_{1-42}$ was also reduced by the treatments, and combination treatment achieve a better efficacy on reducing insoluble $A\beta_{1-42}$ compared to TML-6 or NP106 alone (FIG. 3B). Similar effects of all treatments were found on the reduction of $A\beta_{1-40}$ in the brain homogenates (FIG. 3D) and insoluble $A\beta_{1-40}$ (FIG. 3E). The levels of soluble Aβ species were relatively low (FIGS. 3C, 3F), and combination treatment had the best effect on reducing soluble $A\beta_{1-42}$, albeit not significant.

Example 3 Combination Treatment Improved Nesting Capability, and Nesting Scores Are Highly Correlated with Aβ Loads in the Brain of APP/PS1

Figure 4B:
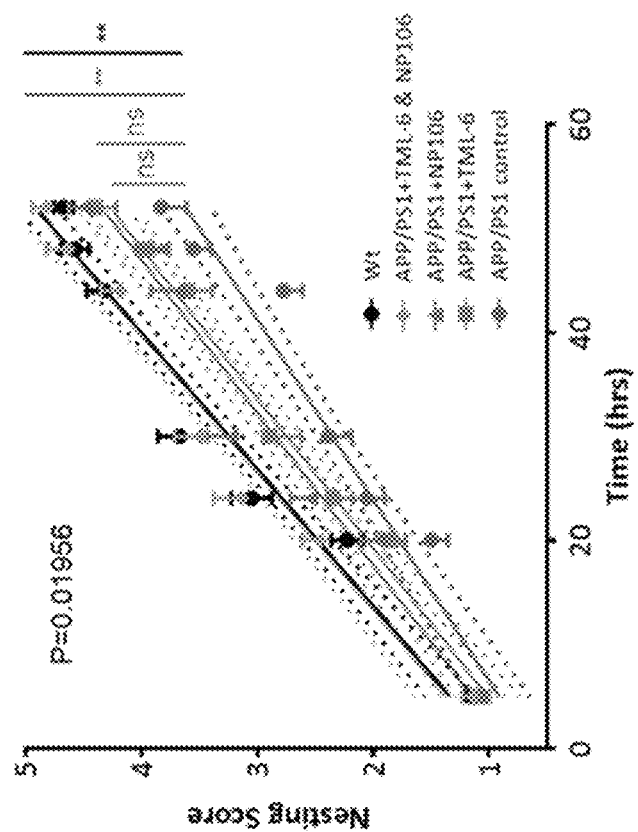
FIGS. 4A to 4C show that nesting capability was synergistically improved by combination treatment, which scores were highly correlated with Aβ loads in the brain of APP/
Figure 4A:
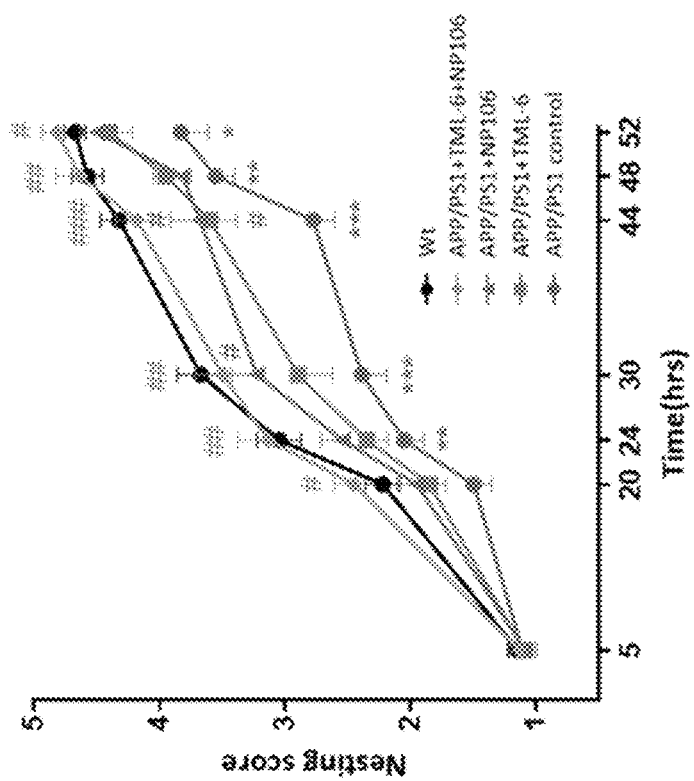

In nesting test, APP/PS1 controls presented a lower nesting score as compared to the wt controls (FIG. 4A), indicating that the neuronal networking in the brain of APP/PS1 mice were dysfunctional. Similar to the beneficial effects on reducing Aβ pathology, two-way ANOVA shows that the treatment using NP106 or TML-6 alone demonstrated significant improvements of nesting scores at indicated time points. Importantly, we observe that a further improvement in APP/PS1 mice with combination treatment to the levels of wt controls. Significant differences between combination treatment group and APP/PS1 controls can be found as early as 20 hr after the test and throughout the entire tests thereafter. The superior effectiveness of combination treatment on the recovery of nesting ability was further supported by the analyses of linear regression (FIG. 4B) showing that the significant difference of the slopes of nesting scores between APP/PS1 controls and wt mice (p<0.01) was completely abolished by combination treatment (p<0.01), but not by TML-6 (p=0.07173) or NP106 alone (p=0.09613). Of note, APP/PS1 mice with combination treatment was reversed to the level of wt (p=1.0), and TML-6 (p=0.1648) or NP106 alone (p=0.121) was also comparable to wt. These data suggest that the abnormal nesting ability in APP/PS1 mice can be improved by either TML-6 or NP106 alone, and a synergistic effect on the slopes of nesting scores was found in mice with combination treatment.

Figure 4C:
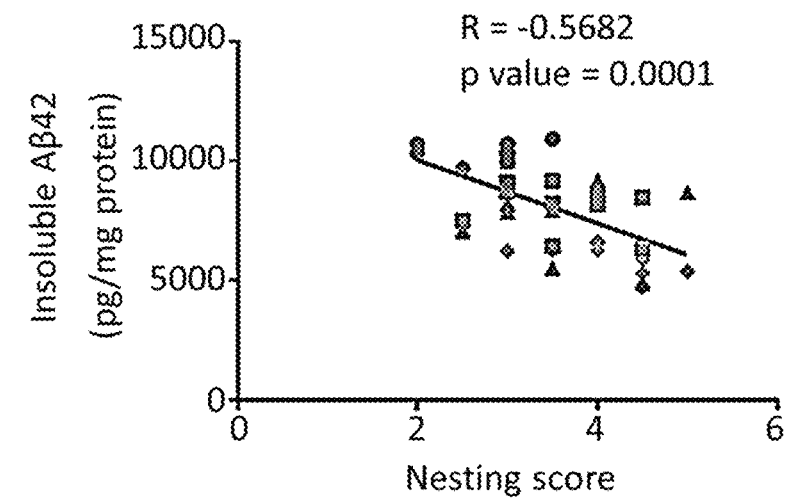
Figure 4C:
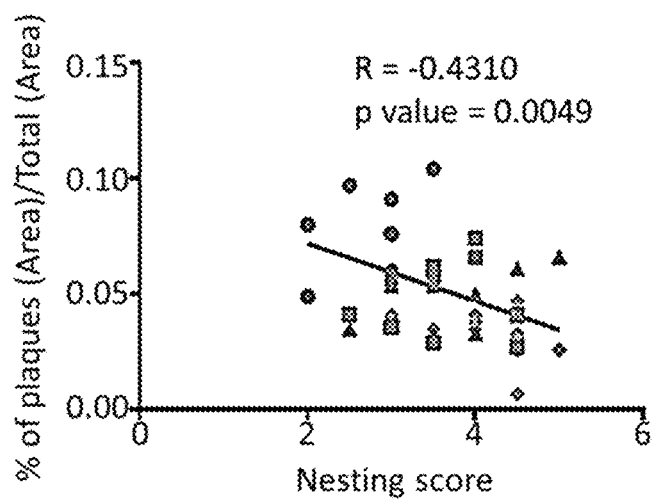
Figure 4C:
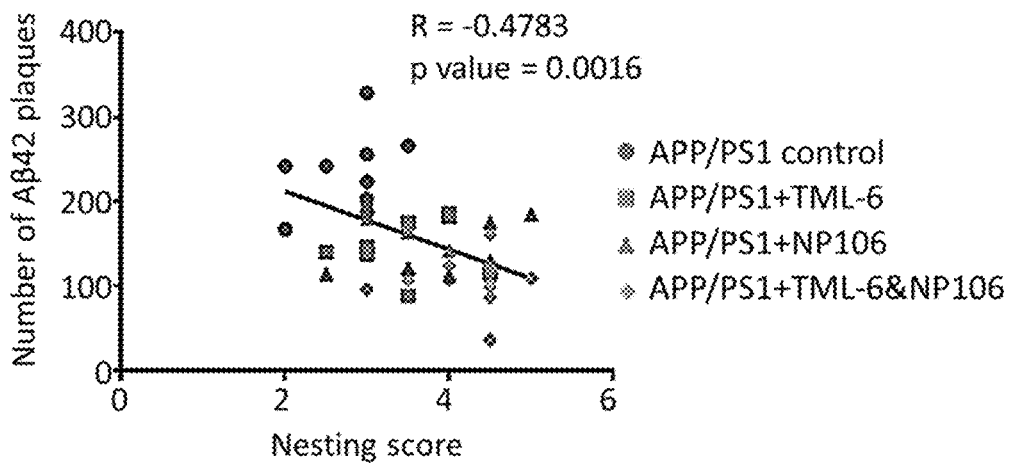

To evaluate the association between nesting ability and Aβ pathologies in the brain, analyses of Spearman correlations between nesting scores at 52 hr and measurements of Aβ pathologies were performed. As shown in FIG. 4C, data indicate that nesting scores were negatively correlated with % of Aβ plaques (r=−0.431, p<0.01), number of Aβ plaques (r=−0.4783, P<0.01), and levels of insoluble $A\beta_{1-42}$ (r=−0.5682, p<0.001). Slightly negative correlations, albeit not significant, were also found in total $A\beta_{1-42}$ (r=−0.2069), soluble $A\beta_{1-42}$ (r=−0.2985), total $A\beta_{1-40}$ (r=−0.1637), and insoluble $A\beta_{1-40}$ (r=−0.1763), but not soluble $A\beta_{1-40}$ (r=0.03743). These findings echo the previous notion that nesting ability is compromised by increasing Aβ pathologies in the brain. Since the age factor was excluded in this study, our data suggest that this nesting test can be a sensitive measurement for the evaluation of the severity of cerebral Aβ pathologies in APP/PS1 mice.

Following nesting tests, mice were then subjected to Morris water maze for tests on spatial learning and memory. Data show that the latency of finding the hidden platform was comparable in all mice at the initial time, which became differentiated between wt and APP/PS1 controls thereafter by two-tailed t-test. These genotype effects on the latency were abolished by treatments with monotherapies or combination treatment showing that the latency of APP/PS1 mice with NP106, TML-6, or combination treatment was comparable to that of wt, and a significant improvement at day2 by NP106 treatment alone as compared to APP/PS1 controls. Analyses of the latency during the training course using linear regression show that slopes of the learning course are comparable among all groups (p=0.9179). In addition, analyses of area under curve (AUC) of the latency during the training courses show that AUC of APP/PS1 controls was significantly increased compared to those of wt mice (p<0.001), which increase was abolished by NP106 alone or combination treatment, but not TML-6 alone. In probe test, duration time in the target quadrant for wt controls tended to be longer than those of APP/PS1 controls, albeit not significant (t-test, p=0.0518), while a significance was found between NP106 treated group and APP/PS1 controls (t-test, p<0.05).

Figure 5A:
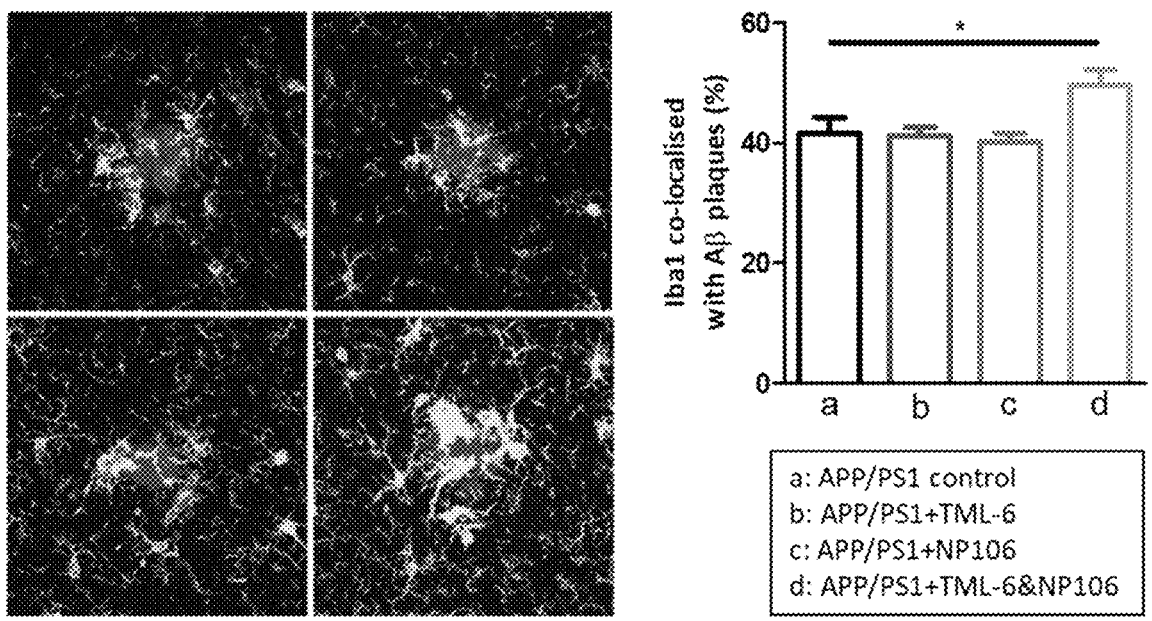
FIGS. 5A to 5I shows that combining NP106 and TML-6 synergistically increased microglial Aβ phagocytosis with significant morphological changes of microglia.
Figure 5B:
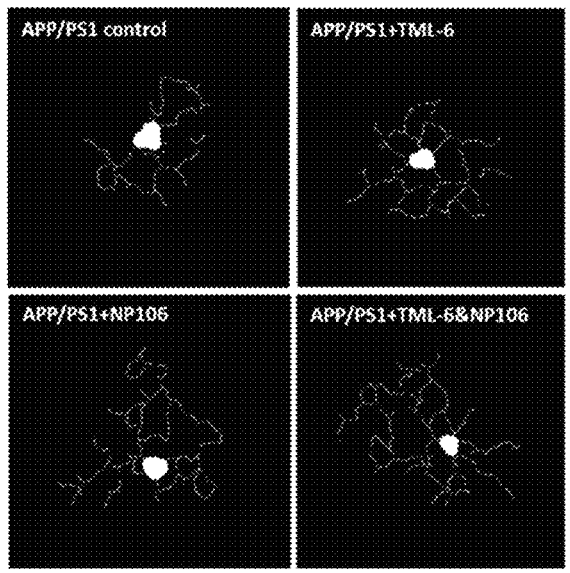
Figure 5C:
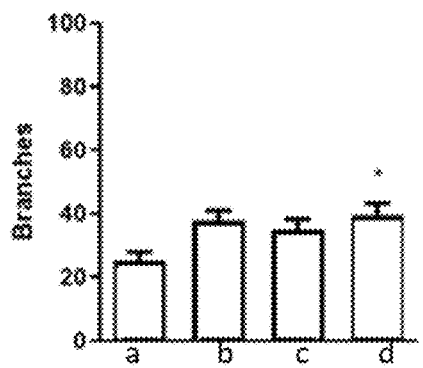
Figure 5D:
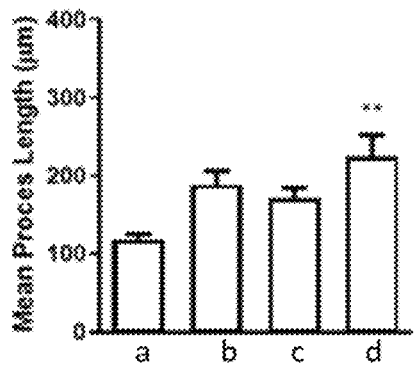
Figure 5E:
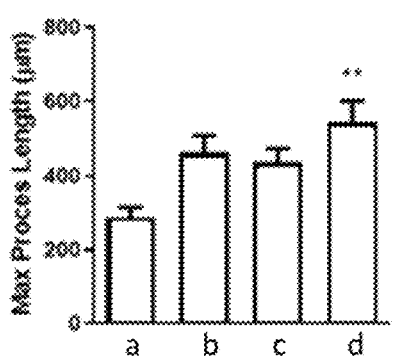
Figure 5F:
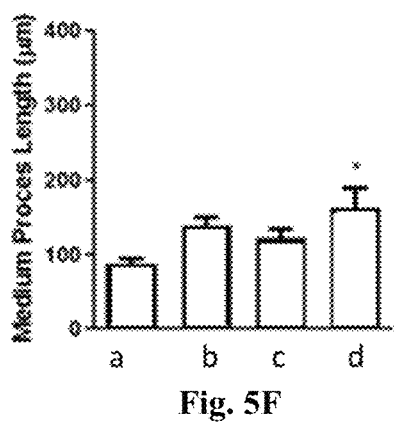
Figure 5G:
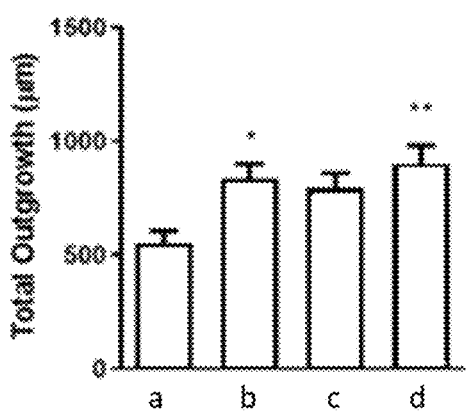
Figure 5H:
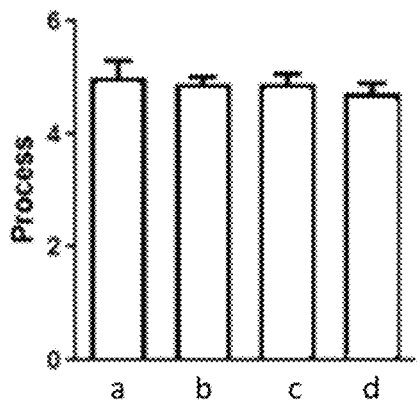
Figure 5I:
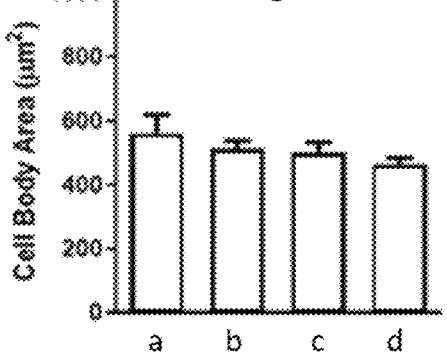

Example 4 Combining NP106 and TML-6 Synergistically Increased Microglial Aβ Phagocytosis Concurrent with Microglial Ramification Since microglia are primary immune cells in the brain responsible for Aβ clearance, treatment effects on microglial Aβ phagocytosis was evaluated by co-localization of microglia and Aβ plaques using confocal microscopy. As shown in FIG. 5A, data suggest that microglial Aβ phagocytosis was not affected by either NP106 or TML-6 alone. However, co-localization of the immunoreactivity of Iba1, a microglial marker, and Aβ plaques in the brain of APP/PS1 mice was significantly elevated in combination treatment group, suggesting that microglial Aβ phagocytosis was synergistically enhanced by combining NP106 and TML-6. Representative skeletonized images from morphological analyses of microglia were presented in FIG. 5B, and quantification using neurite outgrowth analyses further indicate that the number of branches (FIG. 5C) and process length (FIGS. 5D to 5F) of microglia were synergistically increased by combination treatment, but not either alone. Total outgrowth as measured by total length of cell-associated skeletonized outgrowth corrected for diagonal lengths was increased by TML-6 alone and combination treatment (FIG. 5G), while the number of process was comparable among all groups (FIG. 5H). Intriguingly, the cell body size of combination treatment group tended to be smaller than the other groups, albeit not significant (FIG. 5I). These data suggest that combination treatment promoted microglial ramification and drove microglia into a less over-activated state, which is favorable to microglial Aβ phagocytosis.

Example 5 The Aberrant Bacterial Communities in APP/PS1 Mice Was Normalized to Wt Levels by Combining NP106 and TML-6

Figure 6A:
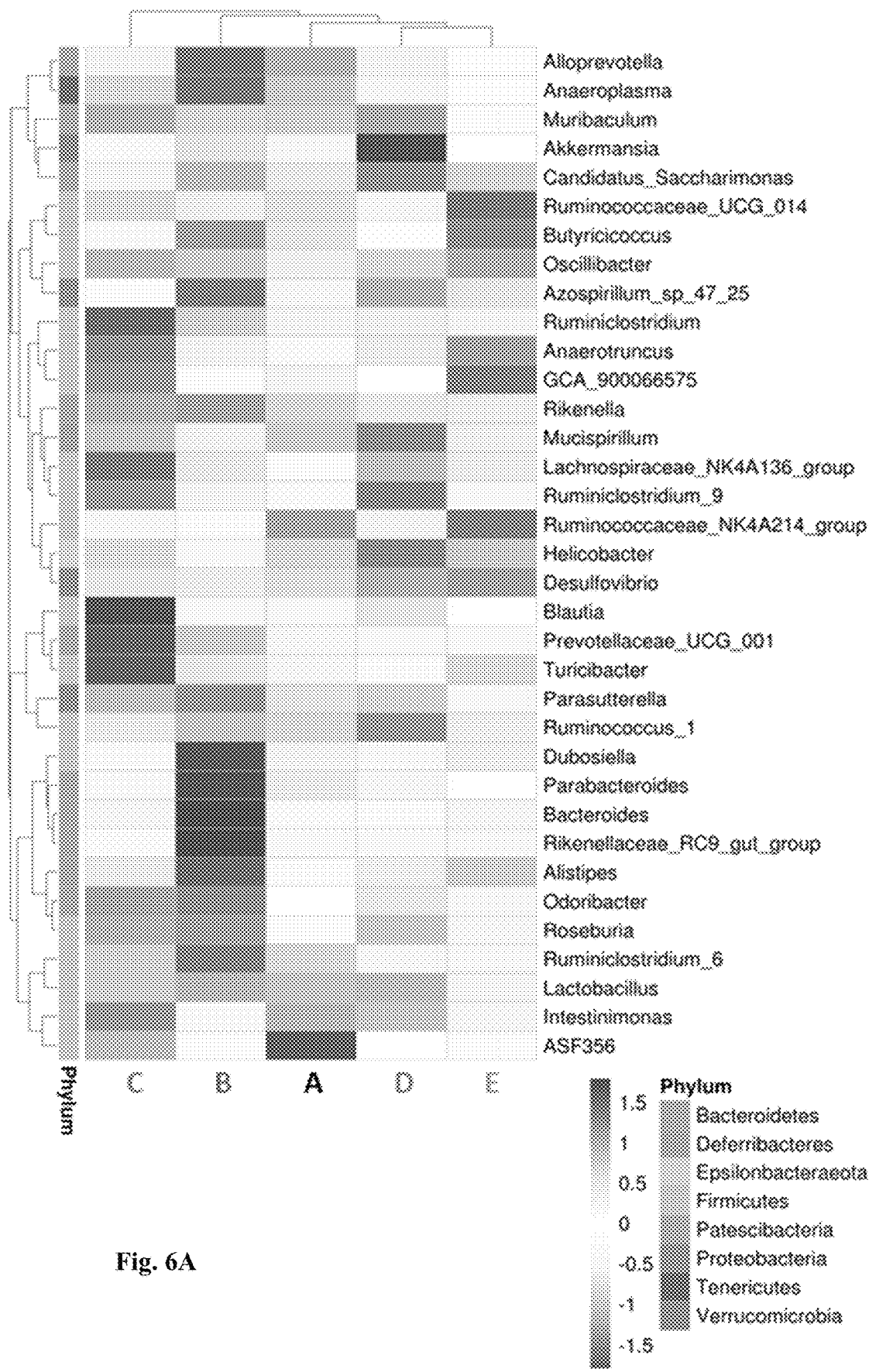
FIGS. 6A to 6C show that the aberrant bacterial communities in APP/PS1 mice was normalized to wt levels by combination treatment.
Figure 6B:
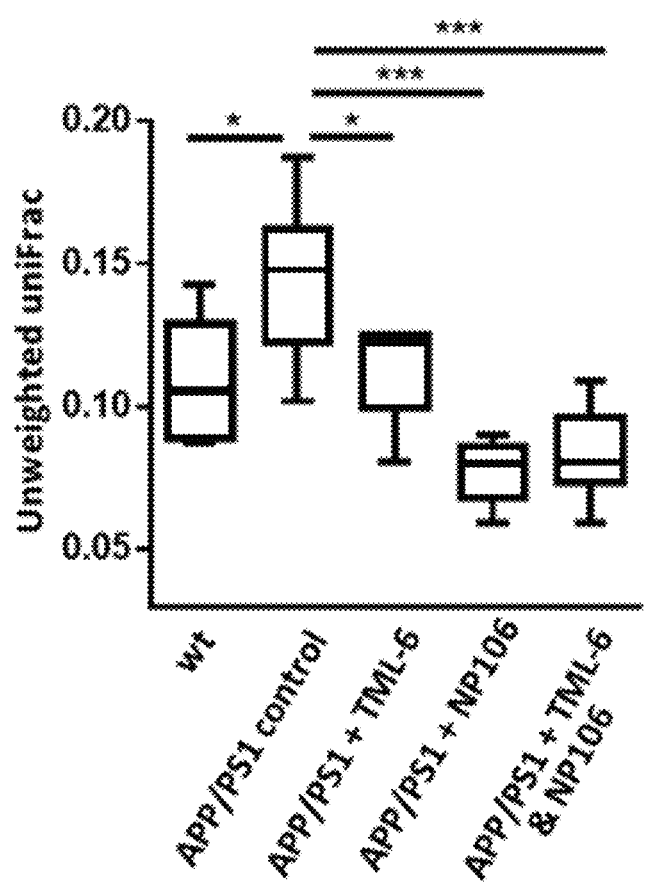
Figure 6C:
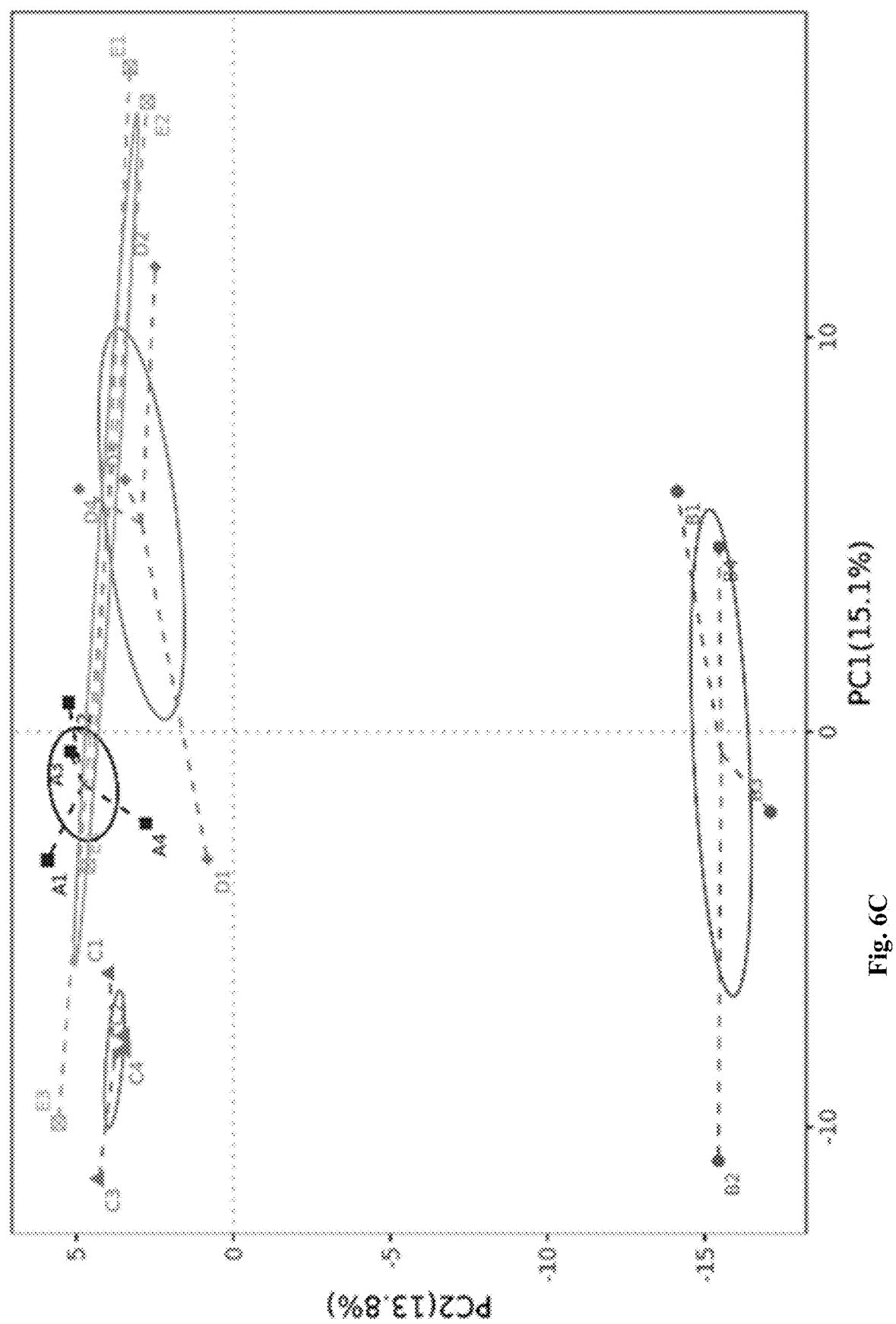

To explore whether the beneficial effects of combination treatment on ameliorating AD-like pathology in APP/PS1 mice are concurrent with the alterations of gut microbiota, fecal analyses using 16S rRNA sequencing from part of animals (n=4 per group) was performed. Cluster heat map of the thirty-five most abundance at genus level is presented to show the similarity of bacterial communities among wt and APP/PS1 mice without or with treatments (FIG. 6A). Data show that APP/PS1 mice with either NP106 or combination treatment tended to have a higher similarity to the wt than APP/PS1 controls. Compared to wt, APP/PS1 controls seemed to have higher levels of *Dubosiella, Parabacteroides, Bacteroides*, and *Rikenellaceae* RC9 gut group, while *Alloprevotella* and *Anaeroplasma* were reduced. These changes can be reversed by all treatments. Analyses of unweighted uniFrac also show the similar findings that the significant structural differences of bacterial communities between APP/PS1 controls and wt can be abolished by all treatments, while APP/PS1 mice with either NP106 or combination treatment were highly significantly different from APP/PS1 controls (FIG. 6B). Principal coordinate analysis (PCoA) of gut bacteria (FIG. 6C) further indicate that the bacterial communities of APP/PS1 mice were different from those of wt and APP/PS1 mice with all treatments, while APP/PS1 mice treated with combination treatment were more similar to those of wt than other treatment groups. As shown in Table 1, the synergistic effects of combination treatment on bacterial communities were supported by the analyses of among-group differences, including analysis of group similarities (ANOSIM), multi-response permutation procedures (MRPP) and non-parametric multivariate analysis of variance (ADONIS). Results show that APP/PS1 mice treated with combination treatment were comparable to wt in ANOSIM (p=0.124), MRPP (p=0.103), and ADONIS (p=0.140), while ADONIS indicated a marginal similarity between mice with NP106 alone and wt (p=0.057). These results suggest that aberrant bacterial communities in APP/PS1 mice was synergistically normalized to the levels of wt by combination treatment, but not either alone.

TABLE 1

Aberrant bacterial communities in APP/PS1 mice was synergistically normalized to the levels of wt by combination treatment, but not either alone. The synergistic effects of combination treatment on bacterial communities were supported by the analyses of among-group differences, including analysis of group similarities (ANOSIM), multi-response permutation procedures (MRPP) and non-parametric multivariate analysis of variance (ADONIS).

| Group | Anosim | | MRPP | | Adonis | |
| --- | --- | --- | --- | --- | --- | --- |
| | R | p value | Expected δ | p value | $R^2$ | p value |
| A vs. B | 1 | 0.028* | 0.42 | 0.041* | 0.53 | 0.026* |
| A vs. C | 0.875 | 0.026* | 0.34 | 0.024* | 0.36 | 0.028* |
| A vs. D | 0.490 | 0.049* | 0.36 | 0.034* | 0.27 | 0.057 |
| A vs. E | 0.281 | 0.124 | 0.35 | 0.103 | 0.22 | 0.140 |
| B vs. C | 1 | 0.029* | 0.44 | 0.030* | 0.62 | 0.028* |
| B vs. D | 0.906 | 0.031* | 0.43 | 0.035* | 0.48 | 0.028* |
| B vs. E | 0.938 | 0.031* | 0.44 | 0.037* | 0.49 | 0.028* |
| C vs. D | 0.865 | 0.026* | 0.39 | 0.022* | 0.43 | 0.026* |
| C vs. E | 0.438 | 0.024* | 0.37 | 0.027* | 0.36 | 0.030* |
| D vs. E | 0.104 | 0.194 | 0.36 | 0.224 | 0.18 | 0.223 |

A, wt;
B, APP/PS1 control;
C, TML-6 alone;
D, NP106 alone;
E, combination treatment.
*p <0.05.

Figure 7A:
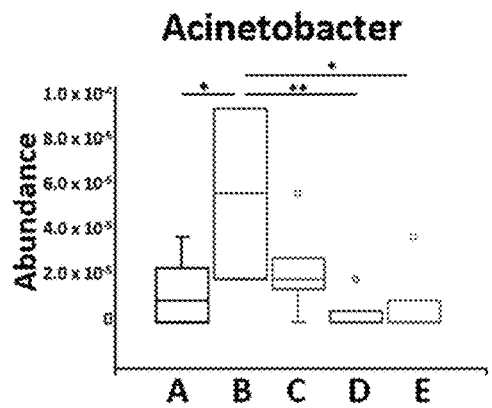
FIGS. 7A to 7P shows that sixteen bacteria genera with p-significance on treatment effects were identified by meta-genomeSeq analyses. Among them, twelve bacteria genera were elevated, and four bacteria genera were reduced in APP/PS1 controls compared to wt. Ten bacteria genera, including *Acinetobacter* (FIG. 7A), *Bacteroides* (FIG. 7B), *Dubosiella* (FIG. 7C), *Eubacterium nodatum* group (FIG. 7D), Family XIII AD3011 group (FIG. 7E), *Gemella* (FIG. 7F), *Lachnospiraceae UCG* 001 (FIG. 7G), *Marinomonas* (FIG. 7I), *Rikenellaceae RC9* gut group (FIG. 7K), and *Vibrio* (FIG. 7J), were significantly increased in APP/PS1 controls, which can be reduced by the treatments at various degrees. In contrast, two bacteria genera, including *Alloprevotella* (FIG. 7M) and *Butyricicoccus* (FIG. 7N), were significantly reduced in APP/PS1 controls, which can be increased by all treatments. The name of genus (g) and the previous family (f) are indicated in each boxplot, and outliers (circle) that their values are outside the interquartile range are indicated. *$p<0.05$; **$p<0.01$.
Figure 7B:
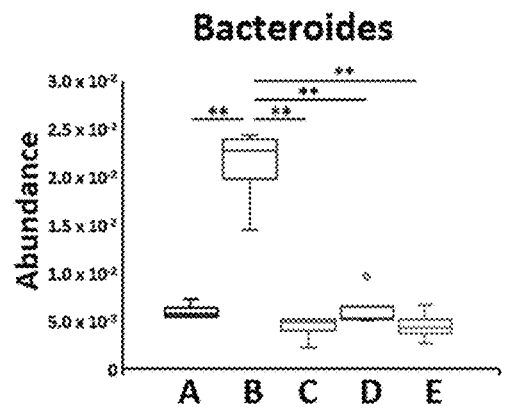
Figure 7C:
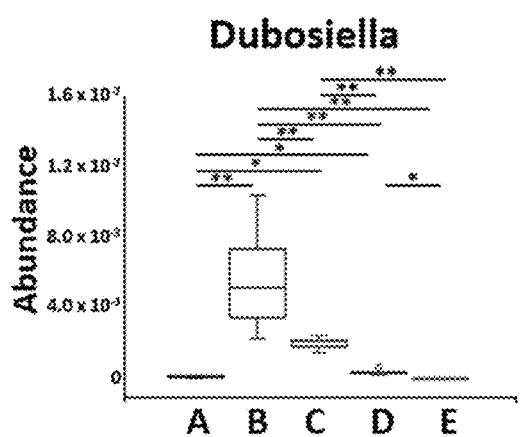
Figure 7D:
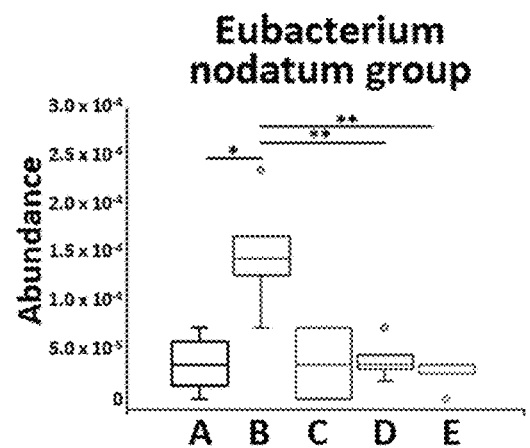
Figure 7E:
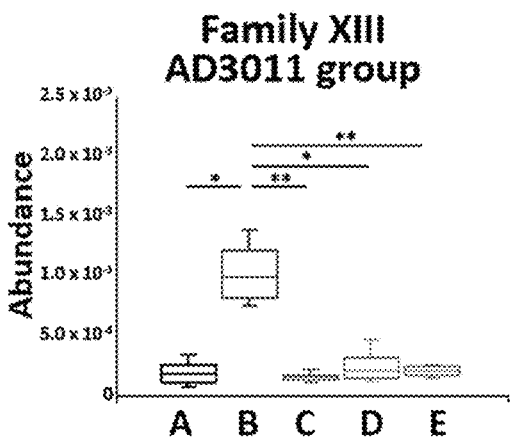
Figure 7F:
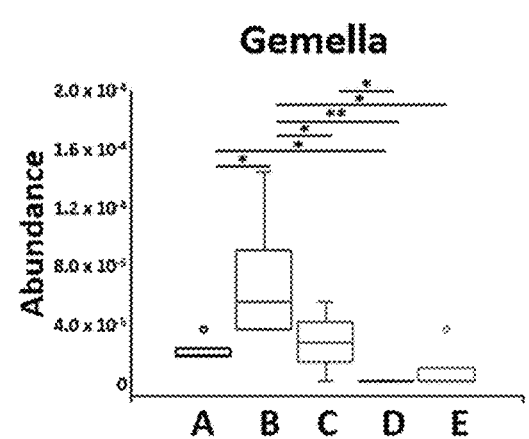
Figure 7G:
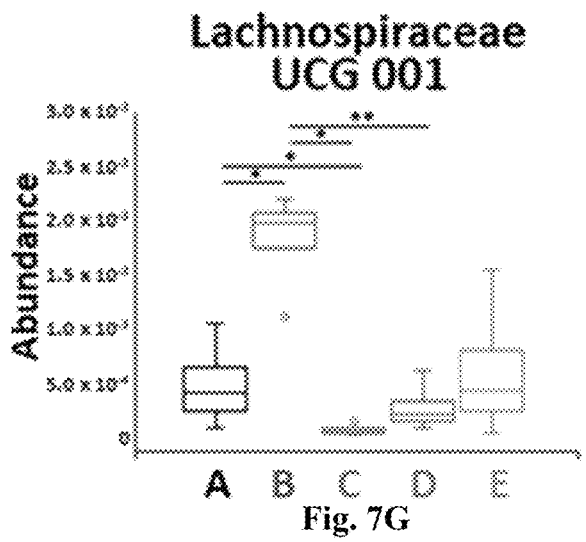
Figure 7H:
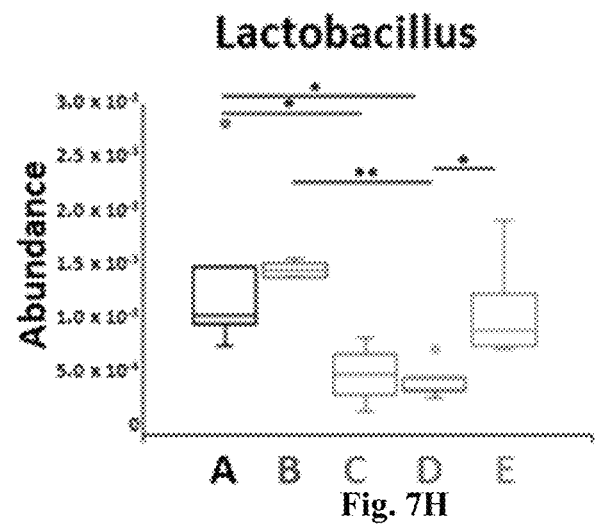
Figure 7I:
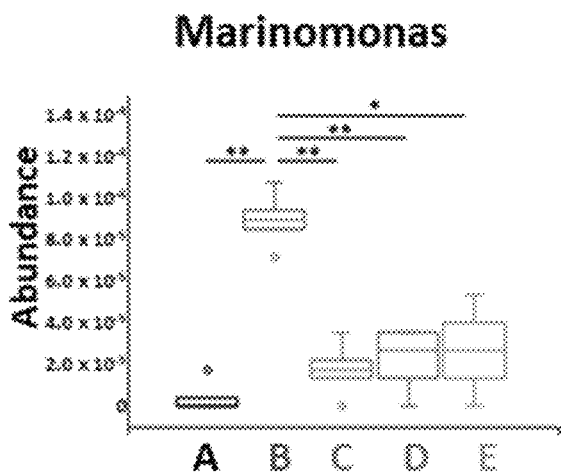
Figure 7J:
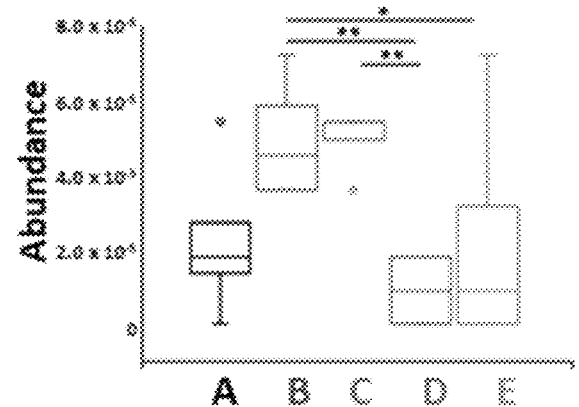
Figure 7K:
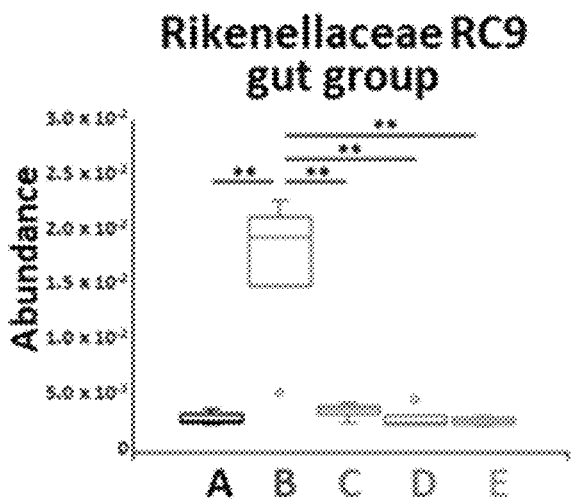
Figure 7L:
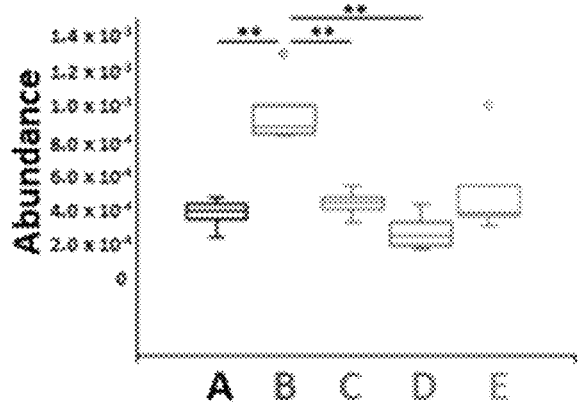
Figure 7M:
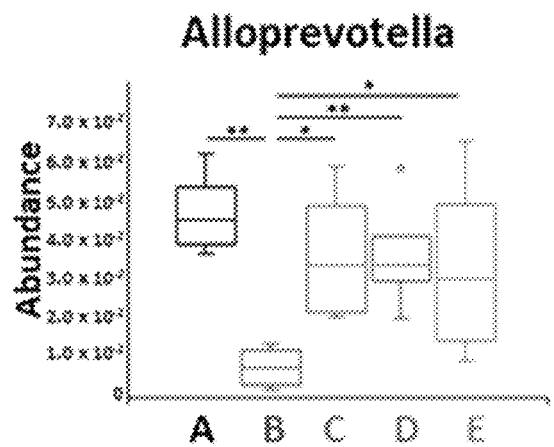
Figure 7N:
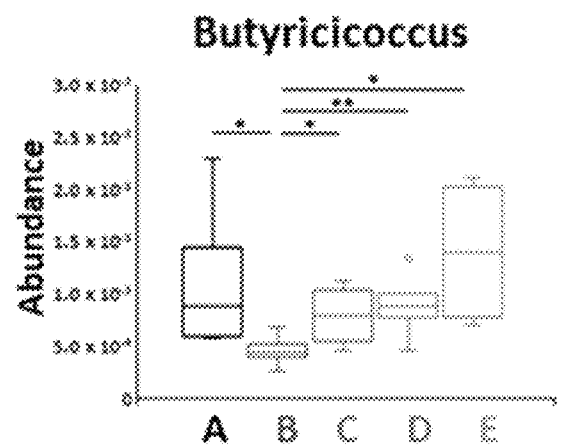
Figure 7O:
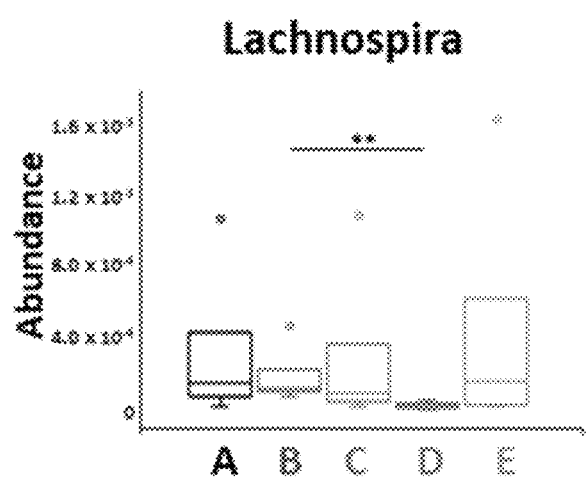
Figure 7P:
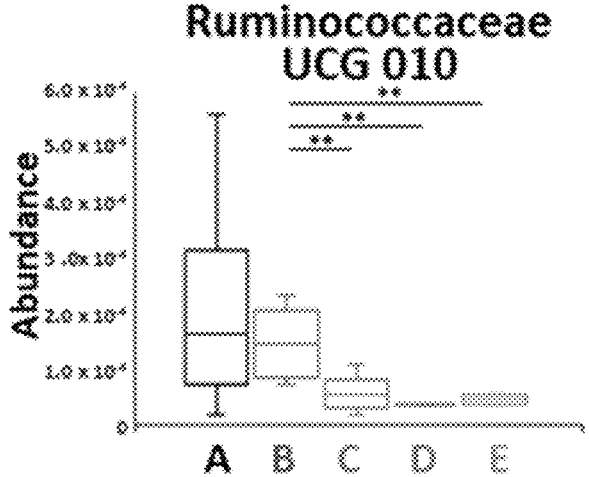

In an attempt to investigate the differential abundance of bacterial genera, we demonstrate sixteen bacteria genera with significant alterations of abundance as determined by the analysis of metagenomeSeq using the q-significance that is normalized from the p-significance. Among them, five bacteria genera, including *Alloprevotella, Bacteroides, Dubosiella, Marinomonas*, and *Rikenellaceae* RC9 gut group, show q-significance between APP/PS1 controls and wt, which were reversed to wt levels by NP106 alone, while combination treatment was effective on *Bacteroides, Dubosiella*, and *Rikenellaceae* RC9 gut group. As shown in FIGS. 7A to 7P, the p-significance of those sixteen bacteria genera show that twelve bacteria genera were elevated, and four bacteria genera were reduced in APP/PS1 controls compared to wt. Among them, ten bacteria genera, including *Acinetobacter, Bacteroides, Dubosiella, Eubacterium nodatum* group, Family XIII AD3011 group, *Gemella, Lachnospiraceae UCG* 001, *Marinomonas, Rikenellaceae RC9* gut group, and *Vibrio*, were significantly increased in APP/PS1 controls, which were somewhat reduced by the treatments. In contrast, two bacteria genera, including *Alloprevotella* and *Butyricicoccus*, were significantly reduced in APP/PS1 controls, which can be increased by all treatments.

Example 6 Seven Bacteria Genera Were Highly Correlated with the Severity of Both Cerebral Aβ Pathology and Nesting Behavioral Abnormality Next, we investigate whether the abundance of the sixteen bacteria genera identified by metagenomeSeq analyses is associated with nesting capability or Aβ pathologies in APP/PS1 mice. Analyses of Spearman correlation using nesting scores and the abundance of the sixteen bacteria genera in corresponding animals demonstrate that eight bacteria genera were highly correlated with nesting performance (Table 2). Among them, seven bacteria genera, including *Acinetobacter* (p<0.05), *Bacteroides* (p<0.05), *Dubosiella* (p<0.001), *Eubacterium nodatum* group (p<0.001), Family XIII AD3011 group (p<0.05), *Marinomonas* (p<0.01), and *Rikenellaceae RC9* gut group (p<0.001), which were increased in APP/PS1 controls as compared to wt were negatively correlated with nesting scores. In contrast, *Butyricicoccus* (p<0.01), which was decreased in APP/PS1 controls, was positively correlated with nesting scores.

TABLE 2

Seven bacteria genera were highly correlated with the severity of both cerebral Aβ pathology and nesting behavioral abnormality. Correlation analyses indicate that the abundance of seven bacteria genera were highly correlated with both nesting scores (Spearman correlation) and at least two measurements of Aβ pathologies (Pearson correlation). Among them, the abundance of six bacteria genera (highlight in blue) were positively correlated with many Aβ pathologies and negatively correlated with nesting scores, while *Butyricicoccus* (highlight in orange), which was decreased in APP/PS1 controls, was positively correlated with nesting scores and negatively correlated with area of Aβ plaques, number of Aβ plaques, and small Aβ plaques.

| | Nesting | | Area of Aβ plaques | | Number of Aβ plaques | | Aβ plaques >500 μm² | | Aβ plaques <500 μm² | |
|---|---|---|---|---|---|---|---|---|---|---|
| | R | P value | R | P value | R | P value | R | P value | R | P value |
| Genera abundance increased in APP/PS1 mice | | | | | | | | | | |
| Acinetobacter | −0.493 | 0.027* | 0.363 | 0.167 | 0.415 | 0.110 | 0.283 | 0.288 | 0.419 | 0.106 |
| Bacteroides | −0.503 | 0.024* | 0.607 | 0.013* | 0.586 | 0.017* | 0.583 | 0.018* | 0.550 | 0.027* |
| Dubosiella | −0.756 | <0.001*** | 0.543 | 0.030* | 0.649 | 0.007** | 0.331 | 0.210 | 0.680 | 0.004** |
| Eubacterium nodatum group | −0.761 | <0.001*** | 0.505 | 0.046* | 0.500 | 0.049* | 0.411 | 0.114 | 0.488 | 0.055 |
| Family XIII AD3011 group | −0.526 | 0.017* | 0.590 | 0.016* | 0.592 | 0.016* | 0.570 | 0.021* | 0.560 | 0.024* |
| Gemella | −0.412 | 0.071 | 0.585 | 0.017* | 0.541 | 0.030* | 0.518 | 0.040* | 0.512 | 0.042* |
| Lachnospiraceae UCG001 | −0.164 | 0.491 | 0.477 | 0.062 | 0.416 | 0.109 | 0.471 | 0.065 | 0.377 | 0.149 |
| Lactobacillus | −0.064 | 0.789 | 0.278 | 0.316 | 0.313 | 0.238 | 0.181 | 0.502 | 0.323 | 0.221 |
| Marinomonas | −0.626 | 0.003** | 0.598 | 0.014* | 0.647 | 0.007** | 0.463 | 0.071 | 0.649 | 0.007** |
| Megasphaera | −0.425 | 0.062 | 0.339 | 0.199 | 0.415 | 0.110 | 0.263 | 0.325 | 0.424 | 0.102 |
| Rikenellaceae RC9 gut group | −0.691 | <0.001*** | 0.592 | 0.030* | 0.502 | 0.048* | 0.536 | 0.032* | 0.462 | 0.072 |
| Vibrio | −0.363 | 0.116 | 0.391 | 0.134 | 0.472 | 0.065 | 0.264 | 0.324 | 0.490 | 0.054 |
| Genera abundance decreased in APP/PS1 mice | | | | | | | | | | |
| Alloprevotella | 0.320 | 0.169 | −0.080 | 0.769 | −0.154 | 0.569 | −0.060 | 0.825 | −0.168 | 0.535 |
| Butyricicoccus | 0.622 | 0.003** | −0.509 | 0.044* | −0.546 | 0.029* | −0.433 | 0.094 | −0.536 | 0.032* |
| Lachnospira | 0.150 | 0.528 | −0.241 | 0.369 | −0.121 | 0.656 | −0.327 | 0.217 | −0.066 | 0.808 |
| Ruminococcaceae UCG 010 | −0.163 | 0.493 | 0.381 | 0.145 | 0.398 | 0.127 | 0.343 | 0.193 | 0.383 | 0.142 |

*p <0.05;
**p <0.01;
***p <0.001.

To correlate the abundance of the sixteen bacteria genera with Aβ pathologies, area of Aβ plaques, number of Aβ plaques, large Aβ plaques (size >500 μm$^2$), and small Aβ plaques (size <500 μm$^2$) were applied. As shown in Table 2, the abundance of seven bacteria genera, including *Bacteroides*, *Dubosiella*, *Eubacterium nodatum* group, Family XIII AD3011 group, *Gemella*, *Marinomonas*, and *Rikenellaceae RC9* gut group, were positively correlated with many Aβ pathologies. As expected, *Butyricicoccus*, which was decreased in APP/PS1 controls, was negatively correlated with area of Aβ plaques, number of Aβ plaques, and small Aβ plaques ($p<0.05$). Taken together, correlation analyses indicate that the abundance of seven bacteria genera were highly correlated with both nesting scores and at least two measurements of Aβ pathologies. Six of them, including *Bacteroides*, *Dubosiella*, *Eubacterium nodatum* group, Family XIII AD3011 group, *Marinomonas*, and *Rikenellaceae RC9* gut group, which were increased in APP/PS1 controls as compared to wt were positively and negatively correlated with Aβ pathologies and nesting scores, respectively. Coherent to its beneficial properties, the abundance of *Butyricicoccus* in APP/PS1 mice, which can be elevated to wt levels by different treatments in varying degrees, was negatively and positively correlated with Aβ pathologies and nesting scores, respectively.

While the present disclosure has been described in conjunction with the specific embodiments set forth above, many alternatives thereto and modifications and variations thereof will be apparent to those of ordinary skill in the art. All such alternatives, modifications and variations are regarded as falling within the scope of the present disclosure.

What is claimed is:

1. A method for preventing, ameliorating and/or treating Alzheimer's disease in a subject in need of such treatment, wherein the method comprises administrating to said subject a pharmaceutical combination comprising an effective amount of TML-6, or a pharmaceutically acceptable salt, solvate, hydrate, isotopologue, or prodrug of TML-6 and an effective amount of an anti-A beta (Aβ) antibody or an antigen-binding fragment thereof and optionally a pharmaceutically acceptable carrier or excipient,

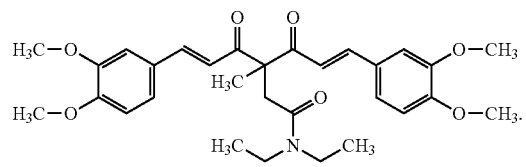

TML-6

2. The method according to claim 1, wherein the TML-6, or the pharmaceutically acceptable salt, solvate, hydrate, isotopologue, or prodrug of TML-6 and the anti-Aβ antibody or the antigen-binding fragment thereof are co-administered simultaneously, separately or sequentially, or co-administered in combination as a coformulation.

3. The method according to claim 1, wherein the anti-Aβ antibody is donanemab, aducanumab, or specifically binds to $Aβ_{1-42}$ or an N-terminal modified form of $Aβ_{1-42}$.

4. The method according to claim 3, wherein the N-terminal modified $Aβ_{1-42}$ is pyro-glutamate Aβ (pE-$Aβ_{3-42}$).

5. The method according to claim 1, wherein the anti-Aβ antibody comprises a light-chain CDR1 (L-CDR1) having the sequence of SEQ ID NO: 1, SEQ ID NO: 7, or SEQ ID NO: 14; a light-chain CDR2 (L-CDR2) having the sequence of SEQ ID NO: 2 or SEQ ID NO: 15; a light-chain CDR3 (L-CDR3) having the sequence of SEQ ID NO: 3, SEQ ID NO: 8, SEQ ID NO: 21, or SEQ ID NO: 24; a heavy-chain CDR1 (H-CDR1) having the sequence of SEQ ID NO: 4, SEQ ID NO: 9, SEQ ID NO: 11, SEQ ID NO: 16, or SEQ ID NO: 25; a heavy-chain CDR2 (H-CDR2) having the sequence of SEQ ID NO: 5, SEQ ID NO: 12, SEQ ID NO: 17, SEQ ID NO: 19, SEQ ID NO: 22, or SEQ ID NO: 26; and a heavy-chain CDR3 (H-CDR3) having the sequence of SEQ ID NO: 6, SEQ ID NO: 10, SEQ ID NO: 13, SEQ ID NO: 18, SEQ ID NO: 20, SEQ ID NO: 23, or SEQ ID NO: 27.

6. The method according to claim 1, wherein the anti-Aβ antibody comprises an H-CDR1 having the sequence of SEQ ID NO: 16, an H-CDR2 having the sequence of SEQ ID NO: 19, an H-CDR3 having the sequence of SEQ ID NO: 20, an L-CDR1 having the sequence of SEQ ID NO: 14, an L-CDR2 having the sequence of SEQ ID NO: 15, and an L-CDR3 having the sequence of SEQ ID NO: 3;
an H-CDR1 having the sequence of SEQ ID NO: 4, an H-CDR2 having the sequence of SEQ ID NO: 5, an H-CDR3 having the sequence of SEQ ID NO: 6, an L-CDR1 having the sequence of SEQ ID NO: 1, an L-CDR2 having the sequence of SEQ ID NO: 2, and an L-CDR3 having the sequence of SEQ ID NO: 3;
an H-CDR1 having the sequence of SEQ ID NO: 9, an H-CDR2 having the sequence of SEQ ID NO: 5, an H-CDR3 having the sequence of SEQ ID NO: 10, an L-CDR1 having the sequence of SEQ ID NO: 7, an L-CDR2 having the sequence of SEQ ID NO: 2, and an L-CDR3 having the sequence of SEQ ID NO: 8;
an H-CDR1 having the sequence of SEQ ID NO: 11, an H-CDR2 having the sequence of SEQ ID NO: 12, an H-CDR3 having the sequence of SEQ ID NO: 13, an L-CDR1 having the sequence of SEQ ID NO: 7, an L-CDR2 having the sequence of SEQ ID NO: 2, and an L-CDR3 having the sequence of SEQ ID NO: 3;
an H-CDR1 having the sequence of SEQ ID NO: 16, an H-CDR2 having the sequence of SEQ ID NO: 17, an H-CDR3 having the sequence of SEQ ID NO: 18, an L-CDR1 having the sequence of SEQ ID NO: 14, an L-CDR2 having the sequence of SEQ ID NO: 15, and an L-CDR3 having the sequence of SEQ ID NO: 3;
an H-CDR1 having the sequence of SEQ ID NO: 9, an H-CDR2 having the sequence of SEQ ID NO: 22, an H-CDR3 having the sequence of SEQ ID NO: 23, an L-CDR1 having the sequence of SEQ ID NO: 7, an L-CDR2 having the sequence of SEQ ID NO: 2, and an L-CDR3 having the sequence of SEQ ID NO: 21; or
an H-CDR1 having the sequence of SEQ ID NO: 25, an H-CDR2 having the sequence of SEQ ID NO: 26, an H-CDR3 having the sequence of SEQ ID NO: 27, an L-CDR1 having the sequence of SEQ ID NO: 7, an L-CDR2 having the sequence of SEQ ID NO: 2, and an L-CDR3 having the sequence of SEQ ID NO: 24.

7. The method according to claim 1, wherein the anti-Aβ antibody is a monoclonal antibody, chimeric antibody, humanized antibody or human antibody.

8. The method according to claim 1, which is for synergistically increasing microglial Aβ phagocytosis, promoting microglial ramification around Aβ plaques, reducing Aβ levels in the brain of the subject, treating a behavioral abnormality, treating aberrant gut microbiota of the subject, and/or reducing a dosage, dose frequency or side effect of the anti-Aβ antibody or an antigen-binding fragment thereof.

9. The method according to claim 8, wherein the side effect comprises amyloid-related imaging abnormalities.

10. A method for reducing a dosage, dose frequency or side effect of a drug for treating Alzheimer's disease in a subject in need of such treatment, wherein the method comprises administrating to said subject an effective amount of TML-6, or a pharmaceutically acceptable salt, solvate, hydrate, isotopologue, or prodrug of TML-6 and optionally a pharmaceutically acceptable carrier or excipient,

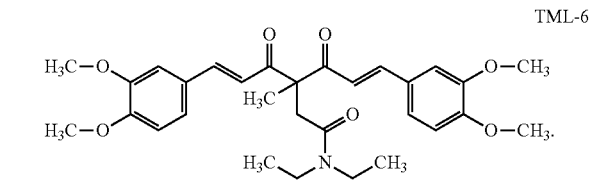 [SMILES: CCN(CC)C(=O)CC(C)(C(=O)/C=C/c1ccc(OC)c(OC)c1)C(=O)/C=C/c1ccc(OC)c(OC)c1]

TML-6

11. The method according to claim 10, wherein the drug for treating Alzheimer's disease comprises an effective amount of an anti-Aβ antibody or an antigen-binding fragment thereof.

12. The method according to claim 10, wherein the TML-6, or the pharmaceutically acceptable salt, solvate, hydrate, isotopologue, or prodrug of TML-6 and the drug for treating Alzheimer's disease are co-administered simultaneously, separately or sequentially, or co-administered in combination as a coformulation.

13. The method according to claim 10, wherein the anti-Aβ antibody is donanemab, aducanumab, or specifically binds to $Aβ_{1-42}$ or an N-terminal modified form of $Aβ_{1-42}$.

14. The method according to claim 13, wherein the N-terminal modified $Aβ_{1-42}$ is pyro-glutamate Aβ (pE-$β_{3-42}$).

15. The method according to claim 10, wherein the anti-Aβ antibody comprises an L-CDR1 having the sequence of SEQ ID NO: 1, SEQ ID NO: 7, or SEQ ID NO: 14; an L-CDR2 having the sequence of SEQ ID NO: 2 or SEQ ID NO: 15; an L-CDR3 having the sequence of SEQ ID NO: 3, SEQ ID NO: 8, SEQ ID NO: 21, or SEQ ID NO: 24; an H-CDR1 having the sequence of SEQ ID NO: 4, SEQ ID NO: 9, SEQ ID NO: 11, SEQ ID NO: 16, or SEQ ID NO: 25; an H-CDR2 having the sequence of SEQ ID NO: 5, SEQ ID NO: 12, SEQ ID NO: 17, SEQ ID NO: 19, SEQ ID NO: 22, or SEQ ID NO: 26; and an H-CDR3 having the sequence of SEQ ID NO: 6, SEQ ID NO: 10, SEQ ID NO: 13, SEQ ID NO: 18, SEQ ID NO: 20, SEQ ID NO: 23, or SEQ ID NO: 27.

16. The method according to claim 10, wherein the anti-Aβ antibody comprises an H-CDR1 having the sequence of SEQ ID NO: 16, an H-CDR2 having the sequence of SEQ ID NO: 19, an H-CDR3 having the sequence of SEQ ID NO: 20, an L-CDR1 having the sequence of SEQ ID NO: 14, an L-CDR2 having the sequence of SEQ ID NO: 15, and an L-CDR3 having the sequence of SEQ ID NO: 3;
   an H-CDR1 having the sequence of SEQ ID NO: 4, an H-CDR2 having the sequence of SEQ ID NO: 5, an H-CDR3 having the sequence of SEQ ID NO: 6, an L-CDR1 having the sequence of SEQ ID NO: 1, an L-CDR2 having the sequence of SEQ ID NO: 2, and an L-CDR3 having the sequence of SEQ ID NO: 3;
   an H-CDR1 having the sequence of SEQ ID NO: 9, an H-CDR2 having the sequence of SEQ ID NO: 5, an H-CDR3 having the sequence of SEQ ID NO: 10, an L-CDR1 having the sequence of SEQ ID NO: 7, an L-CDR2 having the sequence of SEQ ID NO: 2, and an L-CDR3 having the sequence of SEQ ID NO: 8;
   an H-CDR1 having the sequence of SEQ ID NO: 11, an H-CDR2 having the sequence of SEQ ID NO: 12, an H-CDR3 having the sequence of SEQ ID NO: 13, an L-CDR1 having the sequence of SEQ ID NO: 7, an L-CDR2 having the sequence of SEQ ID NO: 2, and an L-CDR3 having the sequence of SEQ ID NO: 3;
   an H-CDR1 having the sequence of SEQ ID NO: 16, an H-CDR2 having the sequence of SEQ ID NO: 17, an H-CDR3 having the sequence of SEQ ID NO: 18, an L-CDR1 having the sequence of SEQ ID NO: 14, an L-CDR2 having the sequence of SEQ ID NO: 15, and an L-CDR3 having the sequence of SEQ ID NO: 3;
   an H-CDR1 having the sequence of SEQ ID NO: 9, an H-CDR2 having the sequence of SEQ ID NO: 22, an H-CDR3 having the sequence of SEQ ID NO: 23, an L-CDR1 having the sequence of SEQ ID NO: 7, an L-CDR2 having the sequence of SEQ ID NO: 2, and an L-CDR3 having the sequence of SEQ ID NO: 21; or
   an H-CDR1 having the sequence of SEQ ID NO: 25, an H-CDR2 having the sequence of SEQ ID NO: 26, an H-CDR3 having the sequence of SEQ ID NO: 27, an L-CDR1 having the sequence of SEQ ID NO: 7, an L-CDR2 having the sequence of SEQ ID NO: 2, and an L-CDR3 having the sequence of SEQ ID NO: 24.

17. The method according to claim 10, wherein the anti-Aβ antibody is a monoclonal antibody, chimeric antibody, humanized antibody or human antibody.

18. The method according to claim 17, wherein the side effect comprises amyloid-related imaging abnormality.

\* \* \* \* \*